United States Patent
Kobayashi et al.

(10) Patent No.: US 9,708,581 B2
(45) Date of Patent: Jul. 18, 2017

(54) STEM CELL SEPARATING MATERIAL AND METHOD OF SEPARATION

(71) Applicant: KANEKA CORPORATION, Osaka-shi, Osaka (JP)

(72) Inventors: Akira Kobayashi, Takasago (JP); Kazuaki Yamamoto, Takasago (JP); Shinya Yoshida, Takasago (JP); Hideo Niwa, Takasago (JP); Naohiro Imai, Takasago (JP); Hirokazu Kurata, Kobe (JP); Yoshiaki Miyamoto, Kobe (JP)

(73) Assignee: KANEKA CORPORATION, Osaka (JP)

( * ) Notice: Subject to any disclaimer, the term of this patent is extended or adjusted under 35 U.S.C. 154(b) by 135 days.

(21) Appl. No.: 14/063,407

(22) Filed: Oct. 25, 2013

(65) Prior Publication Data

US 2014/0141505 A1    May 22, 2014

Related U.S. Application Data

(62) Division of application No. 12/091,029, filed as application No. PCT/JP2006/320956 on Oct. 20, 2006, now Pat. No. 9,057,052.

(30) Foreign Application Priority Data

Oct. 21, 2005 (JP) .................. 2005-307741
Oct. 21, 2005 (JP) .................. 2005-307742
Dec. 15, 2005 (JP) .................. 2005-362413

(51) Int. Cl.
| | | |
|---|---|---|
| *C12M 1/12* | (2006.01) | |
| *C12M 1/00* | (2006.01) | |
| *C12M 1/36* | (2006.01) | |
| *C12N 5/074* | (2010.01) | |
| *B01D 39/16* | (2006.01) | |
| *C12M 1/26* | (2006.01) | |

(52) U.S. Cl.
CPC ....... *C12N 5/0607* (2013.01); *B01D 39/1623* (2013.01); *B01D 39/1692* (2013.01); *C12M 33/14* (2013.01); *C12M 47/02* (2013.01); *B01D 2239/0414* (2013.01)

(58) Field of Classification Search
CPC ............ B01D 39/1623; B01D 39/1692; B01D 2239/0414; C12M 33/14; C12M 47/02
USPC ................. 435/283.1, 286.5, 297.1
See application file for complete search history.

(56) References Cited

U.S. PATENT DOCUMENTS

| | | | |
|---|---|---|---|
| 4,330,410 A | | 5/1982 | Takenaka et al. |
| 4,950,454 A | * | 8/1990 | Masuda et al. ............. 436/177 |
| 5,605,959 A | * | 2/1997 | Moriya et al. ............. 524/853 |
| 2005/0212876 A1 | | 9/2005 | Stellbrink et al. |

FOREIGN PATENT DOCUMENTS

| | | | |
|---|---|---|---|
| EP | 0 155 003 A2 | | 9/1985 |
| JP | 7-265407 A | | 10/1995 |
| JP | 8-108069 A | | 4/1996 |
| JP | 08-108069 A | | 4/1996 |
| JP | 11-266852 A | | 10/1999 |
| JP | 2003-319775 A | | 11/2003 |
| WO | WO 00/29655 | * | 5/2000 |
| WO | 01/83709 A1 | | 11/2001 |
| WO | 03/008592 A1 | | 1/2003 |
| WO | 03/053346 A2 | | 7/2003 |
| WO | 2005/012480 A2 | | 2/2005 |
| WO | 2005/035738 A1 | | 4/2005 |
| WO | 2005/042730 A2 | | 5/2005 |

OTHER PUBLICATIONS

Sanders et al., 2005, Journal of Biomedical Material Research, vol. 72A, p. 335-342.*
Abeyta, et al., Unique gene expression signatures of independently-derived human embryonic stem cell lines, Human Molecular Genetics, vol. 13, No. 6, 2004, p. 601-608.
Allegrucci et al., Differences between human embryonic stem cell lines, Human Reproduction Update, vol. Advance Access published on Aug. 26, 2006, p. 1-18.
Holyoake T. L. et al., Efficient Isolation of Human CD34 Positive Hemopoietic Progenitor Cells by Immune Panning, Stem Cells, vol. 12, p. 114-124, 1994.
Mark F. Pittenger et al, "Multilineage Potential of Adult Human Mesenchymal Stem Cells", Science, Apr. 2, 1999, pp. 143-147, vol. 284.
Pittenger M. F., et al., "Multineage potential of adult human mesenchymal stem cells, Science", Science, 1999, pp. 143-147, vol. 284.
Rao, M. Conserved and divergent paths that regulate self-renewal in mouse and human embryonic stem cells, Developmental Biology, vol. 275, p. 269-286, 2004.
Sato, et al., Molecular signature of human embryonic stem cells and its comparison with the mouse, Developmental Biology, vol. 260, 2003, p. 404-413.
Sekiya I., et al., "In vitro cartilage formation by human adult stem cells from bone marrow stroma defines the sequence of cellular and molecular events during chondrogenesis", Proc. Natl. Avad. Sci., 2002, pp. 4397-4402, vol. 99, No. 7.

* cited by examiner

*Primary Examiner* — Shin Lin Chen
(74) *Attorney, Agent, or Firm* — Sughrue Mion, PLLC

(57) ABSTRACT

The present invention has its object to provide a material for separating stem cell and a filter for separating stem cell, each is capable of selectively separating and recovering, in a simple and easy manner, stem cells from body fluids or biological tissue-derived treated fluids, a method for separating and recovering stem cells, and stem cells obtained by such method. The present invention is a material for separating stem cell which has a density K of $1.0 \times 10^4 \leq K \leq 1.0 \times 10^6$ and a fiber diameter of 3 to 40 μm; a filter for separating stem cell which comprises the material for separating stem cell as packed in a container having a fluid inlet port and a fluid outlet port; a method of separating and recovering stem cells which comprises using the material for separating stem cell or the filter for separating stem cell; and a method of producing a multipotent cell fraction.

6 Claims, 3 Drawing Sheets

Example 1

Example 4

Comp.Ex. 3

Example 5

Ref.Ex. 1

Example 2

Example 3

STEM CELL SEPARATING MATERIAL AND METHOD OF SEPARATION

This is a Divsional of application Ser. No. 12/091,029 filed Jan. 13, 2009, which is a National Stage of International Application No. PCT/JP2006/320956 filed on Oct. 20, 2006, claiming priority based on Japanese Patent Application Nos. 2005-307741, 2005-307742, and 2005-362413, filed Oct. 21, 2005, Oct. 21, 2005, and Dec. 15, 2005, respectively, the contents of all of which are incorporated herein by reference in their entirety.

TECHNICAL FIELD

The present invention relates to a material for separating stem cell and a filter for separating stem cell, each for selectively capturing and recovering stem cells from body fluids such as bone marrow fluid, peripheral blood and umbilical cord blood or from biological tissue-derived fluids obtained after some treatment, and to a method for such recovery treatment and stem cells obtained by such treatment method.

BACKGROUND ART

In recent years, it has been becoming apparent that adherent stem cells capable of differentiating into various tissues such as bones, cartilages, muscles and fats occur in bone marrow fluid, umbilical cord blood and so forth (Patent Document 1; Non-Patent Document 1; Non-Patent Document 2; Non-Patent Document 3). Adherent stem cells are capable of differentiating into a variety of cells and organs and, therefore, it is very important to have a method of efficiently separating and amplifying such cells from the viewpoint of advancement of regenerative medicine. It is reported that the frequency of occurrence of adherent stem cells is very little, namely one per $10^4$ to $10^6$ cells in adult bone marrow fluid (Non-Patent Document 4) and various methods of isolating, concentrating and then recovering adherent stem cell fractions have been investigated. Thus, for example, Pittenger et al. revealed the occurrence of progenitor cells capable of differentiating into fat, cartilages or bone cells in a fraction having a specific gravity of 1.073 as obtained by the Ficoll-Paque fractionation method, one of the density gradient separation methods (Non-Patent Document 4). Sekiya et al. also attempted to cause cells gravitationally fractionated by the Ficoll-Paque fractionation method to differentiate into cartilages (Non-Patent Document 5). Further, Wakitani et al. obtained fractions of cells other than erythrocytes using dextran and attempted to cause those cells to differentiate into cartilages (Non-Patent Document 6). However, the material Ficoll is not a material produced in compliance with the GMP (Good Manufacturing Practice) applicable to drugs and, therefore, cannot be used for actual medical purposes. As for the gravitational sedimentation method using dextran, dextran species produced in compliance with the standards for drugs can be used; however, adherent stem cells are separated, accompanied by other nucleated cells, in a fraction other than the erythrocyte layer and, therefore, that method is not always the best from the viewpoint of separation. Further, these methods require the procedure for washing cells several times using a centrifuge for the separation of cells from the separating liquid, although the rate of recovery of adherent stem cells is high; the procedure is complicated and the procedure is accompanied by the risk of cells being damaged by the centrifugation operation or being contaminated when the procedure is carried out in an open system. Furthermore, under the existing circumstances, no device products are available that do not require any cell washing procedure using a centrifuge or the like but can selectively isolate adherent stem cells. For such reasons, for actual separation and recovery of adherent stem cells, there are a number of reports about the case in which the bone marrow fluid or umbilical cord blood is cultured as such and, then, non-adherent cells are washed off to obtain adherent stem cells (e.g. Non-Patent Document 7).

Further, it is said that, in biological tissues such as, for example, fat, skin, blood vessel, cornea, oral cavity, kidney, liver, pancreas, heart, nerve, muscle, prostate, intestine, amnion, placenta and umbilical cord, there are stem cells from which the respective tissues originate. In recent years, however, it has been revealed that, among these stem cells, there are stem cells capable of differentiating not only into cells of the same tissue system but also into cells of another system (Non-Patent Document 8). For example, it is reported that mesenchymal stem cells collected from adipose tissues can differentiate not only into mature adipocytes but also into bone cells, cartilage cells, myoblasts, vascular endothelial cells and so forth (Non-Patent Document 9 and Non-Patent Document 10) and that dermal stem cells can differentiate into nerve cells, smooth muscle cells, adipocytes and so forth (Non-Patent Document 11). Methods of separating and recovering such biological tissue-derived multipotent stem cells are very important from the viewpoint of advancement of regenerative medicine and have the potential for leading to methods for the radical treatment of intractable stem cell exhaustion diseases, bone diseases, cartilage diseases, ischemic diseases, tissue depressions, cardiac failure and so forth. Methods in wide use for separating and collecting stem cells derived from a biological tissue generally comprise disintegrating the tissue with a digestive enzyme and then recovering cells by centrifugation (Non-Patent Document 8). Various other methods have also been investigated; for example, Hedrick et al. disclose systems and methods for recovering, treating, extracting and concentrating stem cells from adipose tissue in a container system (Patent Document 2) and systems and methods for centrifugally separating and concentrating stem cells from tissues using an automated system (Patent Document 3), among others. Yoshimura et al. disclose a method of collecting adipose tissue-derived stem cells from an aqueous solution layer, which results from liposuction, by the density gradient centrifugation method or by using ASTEC 204 (product of AMCO) (Patent Document 4) and a method of recovering such cells by using various methods, including the use of Ficoll (Patent Document 5). Hatanaka discloses a method which comprises subjecting a suspension of cells liberated from a living body-derived material to density gradient centrifugation and then capturing and recovering a specific type group of cells by passing the relevant fraction through a filter (Patent Document 6). Tabata et al. disclose a method comprising disintegrating an adipose tissue with collagenase and, after centrifugation, allowing cells to adhere to a culture dish to thereby remove leukocytes (Patent Document 7).

Patent Document 1: WO01/83709
Patent Document 2: WO2003/053346
Patent Document 3: WO2005/012480
Patent Document 4: WO2005/042730
Patent Document 5: WO2005/035738
Patent Document 6: Japanese Kokai Publication 2003-319775
Patent Document 7: WO2003/008592

Non-Patent Document 1: Pliard A. et al.: Conversion of an Immortilized Mesodermal Progenitor Cell Towards Osteogenic, Chondrogenic, or Adipogenic Pathways. J. Cell Biol. 130(6): 1461-72 (1995)

Non-Patent Document 2: Mackay A. M. et al.: Chondrogenic differentiation of cultured human mesenchymal Stem Cells from Marrow, Tissue Engineering 4(4): 415-428 (1998)

Non-Patent Document 3: Angele P. et al.: Engineering of Osteochondoral Tissue with Bone Marrow Mesenchymal Progenitor Cells in a Derivatived Hyaluronan Geration Composite Sponge, Tissue Engineering 5(6): 545-553 (1999)

Non-Patent Document 4: Pittenger. et al. Multilineage Potential of Adult Human Mesenchymal Stem Cells, Science 284: 143-147 (1999)

Non-Patent Document 5: Sekiya. et al. In vitro Cartilage Formation by human adult Stem Cells from Bone Marrow Stroma defines the sequence cellular and molecular events during chondrogenesis, Developmental Biology 7(99): 4397-4402(2002)

Non-Patent Document 6: Wakitani. et al. Human autologus culture expanded Bone Marrow Mesenchymal Cell Transplantation for repair of Cartilage defects in Osteoarthritic Knees, OsteoArthritis Reserch Society International (2002) 10, 199-206

Non-Patent Document 7: Tsutsumi. et al. Retention of Multilineage Differentiation Potential of Mesenchymal Cells During Proliferation in Response to FGF, Biochemical and Biophysical Reserch Communications 288, 413-419 (2001)

Non-Patent Document 8: Yasuhiko Tabata: Kokomade Susunda Saisei Iryo no Jissai (Actual State of Regenerative Medicine) (2003)

Non-Patent Document 9: Patricia A. Zuk, et al.: Multilineage cells from human adipose tissue: Implications for cell-based therapies. Tissue Engineering Vol. 7(2): 211-228 (2001)

Non-Patent Document 10: Ying Cao, et al.: Human adipose tissue-derived stem cells differentiate into endothelial cells in vitro and improve postnatal neovascularization in vivo. Biochemical and Biophysical Research Communications 332: 370-379 (2005)

Non-Patent Document 11: Toma J G, et al.: Isolation of multipotent adult stem cells from the dermis of mammalian skin. Nature cell biology 3: 778-784 (2001)

SUMMARY OF THE INVENTION

It is an object of the present invention to provide a material for separating stem cell and a filter for separating stem cell through the use of which it is possible to selectively separate and easily recover stem cells from a body fluid such as bone marrow fluid, peripheral blood or umbilical cord blood or from a biological tissue-derived fluid obtained after some treatment, unlike the prior art technologies mentioned above which cannot attain such separation and recovery, and to provide a method of separating and recovering stem cells using such material for separating stem cell and filter for separating stem cell and, further, to stem cells obtained by such method.

The present inventors made intensive investigations concerning the interactions between adherent stem cells occurring in such a body fluid as bone marrow fluid, peripheral blood or umbilical cord blood and materials for separating stem cell varying in density K, material, mesh opening, fiber diameter, etc. Further, the inventors made intensive investigations concerning the density K, material, mesh opening and fiber diameter, among others, suited for separation of biological tissue-derived stem cells contained in a biological tissue-derived treated fluid from a massive amount of tissue-derived unnecessary or impurity components characteristic of such fluid as resulting from disintegration treatment. As a result, it was surprisingly found that materials for separating stem cell differing in density K and fiber diameter and further in material and mesh opening show great differences in affinity for such stem cells as mentioned above and, when such factors are within respective specific ranges, the rate of separation/recovery of the stem cells becomes very high and the stem cells captured can be recovered by means of a cell recovering fluid in a simple and easy manner and that the stem cells thus recovered are multipotent. Such findings have led to completion of the present invention. It was further found that a filter for separating stem cell comprising a container containing an appropriate material for separating stem cell makes it possible to separate and recover the desired stem cells in a very simple and easy manner and in a closed system, without the necessity of adding a separating agent to the relevant body fluid and without any centrifugation procedure.

Thus, the present invention provides the following.

[1]
A material for separating stem cell
which has a density K of $1.0 \times 10^4 \leq K \leq 1.0 \times 10^6$ and a fiber diameter of 3 to 40 μm.

[2]
The material for separating stem cell as defined above under [1]
which is made of at least one synthetic polymer selected from among polyesters, rayon, polyolefins, vinylon, polystyrene, acrylics, nylons and polyurethanes.

[3]
The material for separating stem cell as defined above under [1] or [2]
which is made of a combination of synthetic polymers, namely a polyester and polypropylene; rayon and a polyolefin; or a polyester, rayon and vinylon.

[4]
The material for separating stem cell as defined above under any of [1] to [3],
wherein the minor axis of each mesh opening is not shorter than 3 μm and the major axis is not longer than 120

[5]
The material for separating stem cell as defined above under any of [1] to [4]
which has the form of a nonwoven fabric.

[6]
The material for separating stem cell as defined above under any of [1] to [5],
wherein the stem cells to be separated thereby are body fluid-derived adherent stem cells.

[7]
The material for separating stem cell as defined above under any of [1] to [6],
wherein the body fluid comprises at least one species selected from among bone marrow fluid, peripheral blood and umbilical cord blood.

[8]
The material for separating stem cell as defined above under [6] or [7],
which substantially allows the passage of erythrocytes and leukocytes therethrough.

[9]
The material for separating stem cell as defined above under any of [1] to [5],
wherein the stem cells are stem cells derived from at least one biological tissue selected from the group consisting of subcutaneous fat, visceral fat, white fat, brown fat, skin and blood vessels.

[10]
The material for separating stem cell as defined above under [9],
which has a density K of $1.0\times10^4 \leq K \leq 2.0\times10^5$.

[11]
A filter for separating stem cell
which comprises the material for separating stem cell as defined above under any of [1] to [10] as packed in a container having a fluid inlet port and a fluid outlet port.

[12]
The filter for separating stem cell as defined above under [11],
wherein a washing fluid inlet is provided at the fluid inlet port or on the fluid inlet side other than the fluid inlet port for washing away unnecessary cells and other unnecessary substances remaining in the material for separating stem cell and a cell recovering fluid inlet is provided at the fluid outlet port or at a site on the fluid outlet side other than the fluid outlet port for recovering cells captured by the material for separating stem cell.

[13]
The filter for separating stem cell as defined above under [12],
wherein a bag for receiving and storing a cell recovering fluid containing cells captured by the material for separating stem cell is provided at the fluid inlet port or washing fluid inlet or at a site on the fluid inlet side other than the fluid inlet port or washing fluid inlet.

[14]
The filter for separating stem cell as defined above under [13],
wherein the bag for receiving and storing a cell recovering fluid containing cells captured by the material for separating stem cell is a bag allowing cell culture.

[15]
A method of separating and recovering stem cells from a body fluid or a biological tissue-derived treated fluid
which comprises using the material for separating stem cell as defined above under any of [1] to [10] or the filter for separating stem cell as defined above under any of [11] to [14].

[16]
A method of recovering stem cells,
wherein a body fluid or biological tissue-derived treated fluid is introduced into the filter for separating stem cell as defined above in any of [11] to [14] through the fluid inlet port thereof, a washing fluid is caused to flow from the fluid inlet side for washing and then a cell recovering fluid is caused to flow from the fluid outlet side to thereby recover stem cells captured by the material for separating stem cell.

[17]
The method of recovering stem cells as defined above under [16],
wherein the body fluid comprises at least one species selected from among bone marrow fluid, peripheral blood and umbilical cord blood.

[18]
The method of recovering stem cells as defined above under [16],
wherein the biological tissue-derived treated fluid is a treated fluid obtained by disintegration of at least one biological tissue selected from the group consisting of subcutaneous fat, visceral fat, white fat, brown fat, skin and blood vessels.

[19]
The method of recovering stem cells as defined above under any of [16] to [18],
wherein the body fluid or biological tissue is of the mammalian origin.

[20]
A method of producing a multipotent cell fraction,
wherein the stem cells recovered by the method of recovering stem cells as defined above under any of [16] to [19] are further amplified.

[21]
A stem cell obtained by the method of recovering stem cells as defined above under any of [16] to [19].

DETAILED DESCRIPTION OF THE INVENTION

In the following, the invention is described in detail.
The material for separating stem cell according to the invention has a density K of $1.0\times10^4 \leq K \leq 1.0\times10^6$ and a fiber diameter of 3 to 40 µm.

The stem cells are not particularly restricted but include, as preferred ones, body fluid-derived adherent stem cells and biological tissue-derived stem cells, among others.

The material for separating stem cell according to the invention can capture adherent stem cells, which are useful cells, when a body fluid is passed through the same, upon which such unnecessary cells as erythrocytes, leukocytes and platelets pass through the same. Then, a washing fluid for washing away unnecessary cells remaining in the material for separating stem cell is passed through the material in the same direction as the direction of passage of the body fluid, whereby the erythrocytes, leukocytes and platelets remaining in the material for separating stem cell can be washed away. Further, a recovering fluid for recovering the desired cells is passed through the material in the reverse direction relative to the direction of passage of the body fluid and washing fluid, whereby adherent stem cells can be separated and recovered in high yields in a simple and easy manner.

The term "body fluid" as used herein indicates an adherent stem cell-containing one, such as blood (including peripheral blood and G-CSF mobilized peripheral blood), bone marrow fluid or umbilical cord blood.

The body fluid so referred to herein also includes dilutions of the body fluids mentioned above; and cell suspensions prepared by pretreating the above-mentioned body fluids by density gradient centrifugation using Ficoll, Percoll, hydroxyethylstarch (HES), Vacutainer tube, Lymphoprep or the like.

The term "adherent stem cells" as used herein indicates cells characterized by their ability to adhere to a culture dish and grow and their multipotence. More specifically, the term indicates such multipotent cells as mesenchymal stem cells, multipotent adult progenitor cells (MAPCs), and bone marrow stromal cells, among others.

The term "mesenchymal stem cells" indicates cells separated from a body fluid and capable of repeating self-replication and capable of differentiating into downstream lineage cells. The mesenchymal stem cells are cells capable of differentiating, under the action of a differentiation inducing factor, into mesodermal cells, for example osteoblasts, chondrocytes, vascular endothelial cells or myocardial cells, or adipocytes, cementoblasts or periodontal ligament fibroblasts, which are peridontium-constituting cells. When transplanted into the cardiac muscle in the case of myocardial infarction or dilated cardiomyopathy, they differentiate into the cardiac muscle and, through the excretion of such a cytokine as VEGF, they produce the cardiac muscle protecting and heart function improving effects. Reportedly, rat bone marrow-derived mesenchymal stem cells, when transplanted into the cardiac muscle in a dilated cardiomyopathy model, differentiate into the cardiac muscle and vascular endothelial cells in 5 weeks, increasing the blood vessel density, inhibiting fibrogenesis and improving the heart function (Nagaya N et al. Circulation. 2005 Aug. 23; 112 (8):1128-35), (Nagaya N et al. Am J Physiol Heart Circ Physiol (Jul. 29, 2004). 10, 1125).

When human mesenchymal stem cells are used, the same effects as mentioned above are observed. Thus, human bone marrow-derived mesenchymal stem cells, when transplanted into the murine cardiac muscle, differentiate into the cardiac muscle and express cardiac muscle-specific proteins such as desmin, beta-myosin heavy chain, alpha-actinin, cardiac muscle troponin T and phospholamban (Toma C et al. Circulation. 2002 Jan. 1; 105(1):93-8). When human mesenchymal stem cells are transplanted into a swine cardiac infarction lesion, they are successfully accepted, alpha-myosin heavy chain- and troponin I-positive cardiac muscles are expressed and a heart function-improving effect is produced (Min J Y Ann Thorac Surg. 2002 November; 74(5): 1568-75). Further, when human mesenchymal stem cells in which the cardiac muscle pacemaker gene mHCN2 is expressed are transplanted into the canine cardiac muscle, they transducer electric signals (Potapova I et al. Circ Res. 2004 Apr. 16; 94(7):952-9). As mentioned above, improvements in heart function in cardiac diseases can be brought about by transplantation of mesenchymal stem cells.

Multipotent adult stem cells include, but are not limited to, cells possibly differentiating, under the action of a differentiation inducing factor, into cells other than mesodermal ones, for example into nerve cells or hepatocytes as well.

The term "bone marrow stromal cells" indicates all adherent cell components among bone marrow cells excluding immature and mature blood cells. The characteristic cell surface antigens common to the above-mentioned adherent stem cells include, but are not limited herein in the present invention to, CD13, 29, 44, 49b, 49d, 49e, 71, 73, 90, 105, 166, class I MHC and class II MHC, among others.

As the culture dish so referred to herein, there may be mentioned, among others, polystyrene-made cell culture dishes and flasks generally used for cell culture. The dishes or flasks may be coated with such an extracellular matrix component protein as collagen, fibronectin or laminin, or such a polysaccharide as hyaluronic acid chondroitin sulfate or dermatan sulfate.

By passing a biological tissue-derived treated fluid (i.e. treated fluid containing a biological tissue) through the material for separating stem cell according to the invention, it is possible to capture biological tissue-derived stem cells, which are useful cells, while such tissue-derived impurities as fat droplets, erythrocytes, leukocytes and platelets as well as the enzyme used for disintegration and other unnecessary substances pass through the material. Then, a washing fluid is passed through the material in the same direction as the direction of passage of the treated fluid for washing away unnecessary matters remaining in the material for separating stem cell. After washing away such tissue-derived impurities as fat droplets, erythrocytes, leukocytes and platelets as well as the enzyme used for disintegration and other unnecessary substances remaining in the material for separating stem cell, a fluid for recovering the desired cells is passed through the material in the reverse direction relative to the direction of passage of the treated fluid and washing fluid, whereby the biological tissue-derived stem cells can be recovered in a simple and easy manner and in high yields.

The biological tissue-derived treated fluid, so referred to herein, is, for example, a treated fluid derived from a biological tissue by enzymatic disintegration (enzymatic disintegration-treated fluid), a treated fluid resulting from disintegration by disruption (disruption-treated fluid), a treated fluid resulting from disintegration by abrasion (abrasion-treated fluid), a treated fluid resulting from disintegration by shake extraction (shake extraction-treated fluid) or a treated fluid resulting from disintegration by the liposuction technique which is practiced in cosmetic surgery (liposuction-treated fluid). The biological tissue-derived treated fluid may be one obtained by singly using one of such disintegration methods as given above or by using a combination of two or more of such methods. It may also be a concentrated suspension prepared by a combination of one or more of such methods and a centrifugation procedure.

More specifically, the "enzymatic disintegration-treated fluid" means a treated fluid derived from a biological tissue by disintegration with one or a combination of such digestive enzymes as collagenase, metalloprotease, dispase, trypsin, chymotrypsin, hyaluronidase, pepsin, aminopeptidase, lipase, amylase, and recombinants thereof. The disintegration can be accomplished in an aqueous solution at an arbitrary concentration and at an arbitrary temperature. The use of collagenase, metalloprotease, dispase or trypsin as the digestive enzyme is preferred from the viewpoint of lowly invasive disintegration of a biological tissue in a short period of time.

The "disruption-treated fluid" means a treated fluid resulting from disintegration, in an aqueous solution, of a biological tissue by means of ultrasonic waves or by finely disrupting the biological tissue with a sharp-edged instrument, for instance.

The "abrasion-treated fluid" means a treated fluid resulting from disruption of a biological tissue using a strainer or the like.

The "shake extraction-treated fluid" means a biological tissue-containing treated fluid prepared by vigorously shaking the biological tissue in an aqueous solution.

The "liposuction-treated fluid" means a treated fluid obtained by collecting and disintegrating such a biological tissue as fat by ultrasonic liposuction, powered liposuction, syringe liposuction or a like ordinary method used in cosmetic plastic surgery.

Where appropriate, such a procedure as centrifugation may be combined with these methods. For example, the treated fluid may be the fluid (concentrated suspension) obtained by the procedure comprising centrifuging an enzymatic disintegration-treated fluid, discarding the supernatant after sedimentation of the cells contained therein, and suspending the settled cell mass in a buffer solution, for instance.

However, the biological tissue-derived treated fluid to be used in the practice of the invention is not limited to those mentioned above but may also be a dilution of any of the biological tissue-derived treated fluids mentioned above; or a biological tissue-containing cell suspension prepared by pretreatment of any of the biological tissue-derived treated fluids mentioned above by the density gradient centrifugation technique using Ficoll, Percoll, hydroxyethylstarch (HES), Vacutainer tube, Lymphoprep or the like.

The "biological tissue", so referred to herein, includes all biological tissues containing biological tissue-derived stem cells (i.e. stem cells derived from biological tissues), excluding body fluids. More specifically, it includes subcutaneous fat, visceral fat, white fat, brown fat, skin, blood vessels, cornea, oral cavity, kidney, liver, pancreas, heart, nerves, muscles, prostate, intestines, amnion, placenta, umbilical cord, etc. One or a mixture of subcutaneous fat, visceral fat, white fat, brown fat, skin and blood vessels is preferred from the viewpoint that it contains biological tissue-derived stem cells abundantly. While the term "biological tissue" as used herein does not include, within the meaning thereof, such body fluids themselves as peripheral blood, bone marrow fluid and umbilical cord blood, each biological tissue may contain a small proportion of a body fluid or fluids.

The "biological tissue-derived stem cells" so referred to herein are multipotent cells capable of adhering to a culture dish and thereafter proliferating while forming colonies or clusters or capable of amplifying on a feeder layer while forming colonies or clusters. More specifically, the term indicates stem cells from which tissues are originated, such as adipose tissue-derived mesenchymal stem cells, adipose tissue-derived interstitial stem cells, epidermal stem cells, dermal stem cells, vascular endothelial stem cells, corneal ring stem cells, oral epithelial stem cells, kidney somatic stem cells, liver stem cells, stem cells among pancreatic β cells, heart stem cells, nerve stem cells, muscle stem cells, prostate stem cells, intestinal tract epithelial cells, amnion-derived mesenchymal stem cells, placenta-derived mesenchymal stem cells and umbilical cord-derived mesenchymal stem cells. These stem cells have the ability to repeat self-replication and are cells capable of differentiating into downstream lineage cells. They are cells having the ability to differentiate not only into cells of the original lineage thereof but also into cells of another lineage. The "culture dish" so referred to herein includes the same ones as mentioned hereinabove.

The term "tissue-derived impurities" so referred to herein indicates biological tissue-derived components, other than biological tissue-derived stem cell, as resulting from disintegration of the biological tissue by any of the techniques mentioned above. More specifically, the term includes, within the meaning thereof, tissue constituent collagen, polysaccharides, lipids, membrane constituents, complexes thereof and decomposition products derived therefrom, insoluble residues thereof and, further, erythrocytes, leukocytes, platelets and the like contained in the biological tissue. The "fat droplets" so referred to herein indicate lipid-derived oily droplets formed upon disintegration of a biological tissue, which can be readily identified by observation of the biological tissue-derived treated fluid under a microscope, for instance.

The material for the manufacture of the material for separating stem cell according to the invention preferably comprises at least one species selected from among polyolefins such as polypropylene, polyethylene, high-density polyethylene and low-density polyethylene, polyesters, poly(vinyl chloride), poly(vinyl alcohol), poly(vinylidene chloride), rayon, vinylon, polystyrene, acrylics [poly(methyl methacrylate), poly(hydroxyethyl methacrylate), polyacrylonitrile, poly(acrylic acid), polyacrylates, etc.], nylons, polyurethanes, polyimides, aramides, polyamides, cupra, Kevlar, carbon, phenolic resins, Tetron, pulps, linen, cellulose, kenaf, chitin, chitosan, glasses, cotton and the like. More preferably, it comprises at least one synthetic polymer selected from among polyesters, polystyrene, acrylics, rayons, polyolefins, vinylon, nylons and polyurethanes, among others.

In cases where two or more synthetic polymer species are used in combination, the combination is not particularly restricted but preferably is a combination of a polyester and polypropylene; of rayon and a polyolefin; or of a polyester, rayon and vinylon, for instance.

When two or more synthetic polymer species are used in combination to produce fibers, the form of the fibers may be such that each of the fibers is composed of different synthetic polymer components or the fibers occur as split fibers resulting from peeling and splitting into fibers differing in component material. Further, the fibers may also be ones resulting from conjugation of different single polymer fiber species respectively made of different synthetic polymers. The conjugation so referred to herein is not particularly restricted but refers, among others, to the form constituted of two or more fiber species in a mixed up state or the form resulting from sticking together different fiber forms each made of a single synthetic polymer. The invention is not restricted to these forms, however.

The material for separating stem cell is not particularly restricted in form or shape but includes porous materials having a communicating pore structure, fiber aggregates and woven fabrics. It is preferably constituted of fibers and, more preferably, is a nonwoven fabric.

The material for separating stem cell according to the invention is required to have a density K, namely basis weight $(g/m^2)$/thickness (m) of $1.0 \times 10^4 \leq K \leq 1.0 \times 10^6$ from the viewpoint of the efficiency of removal of erythrocytes, leukocytes and platelets, among others, and of the rate of recovery of the desired cells. From the viewpoint of efficiency of removal of erythrocytes, leukocytes and platelets, among others, the density is preferably $2.5 \times 10^4 \leq K \leq 7.5 \times 10^5$, more preferably $5.0 \times 10^4 \leq K \leq 5.0 \times 10^5$.

When a biological tissue-derived treated fluid is used, the density K of the material for separating stem cell preferably satisfies the condition $1.0 \times 10^4 \leq K \leq 2.0 \times 10^5$. When the density K is in excess of $2.0 \times 10^5$, clogging due to tissue-derived impurities or fat droplets tends to readily occur and, when it is lower than $1.0 \times 10^4$, the rate of capturing of the desired cells tends to become low. From the viewpoint of the rate of removal of tissue-derived impurities such as fat droplets, erythrocytes, leukocytes and platelets and of clogging, the density K is more preferably $2.5 \times 10^4 \leq K \leq 1.95 \times 10^5$, still more preferably $5.0 \times 10^4 \leq K \leq 1.9 \times 10^5$.

The density K is defined as "basis weight $(g/m^2)$/thickness (m)" and can also be expressed as "weight (g)/unit volume $(m^3)$". Therefore, the density K can be determined by measuring the weight (g) per unit volume $(m^3)$ of the material for separating stem cell, irrespective of the form of the material for separating stem cell. On the occasion of measurement, the material should be measured in an undeformed condition, for example without pressurization. Thickness measurements in a non-contact condition can be carried out using a CCD laser azimuth sensor (Keyence model LK-035), for instance.

In cases where the basis weight and thickness are described, for example, in a catalog or manual of the material employed, they may be used as such to calculate the density K according to the formula (basis weight $(g/m^2)$/thickness (m)).

From the viewpoint of the rate of recovery of the desired cells, it is necessary that the material for separating stem cell have a fiber diameter of 3 to 40 μm. When the fiber diameter is smaller than 3 μm, the interaction between the material and leukocytes increases, the rate of removal of erythrocytes, leukocytes and platelets becomes low and clogging with tissue-derived impurities, in particular fat droplets, tends to occur with ease. When it is larger than 40 µm, the effective contact surface area tends to become smaller and short passes may occur with ease, often leading to decreases in the rate of recovery of the desired cells. For strengthening the interaction between the desired cells and the material for separating stem cell, increasing the recovery rate and suppressing the interaction with tissue-derived impurities, especially with fat droplets, the fiber diameter is preferably 3 µm to 35 µm, more preferably 5 µm to 35 µm, still more preferably 5 µm to 30 µm.

When the material for separating stem cell is constituted of fibers, the fiber diameter can be determined, for example, by photographing the material for separating stem cell using a scanning electron microscope, measuring at least 30 arbitrarily selected points, and calculating the mean of the fiber diameter values calculated based on the scale appearing on the photograph. When the material for separating stem cell is a porous body, the term "fiber diameter" means the average width of the resin portions (non-pore portions) in the cross section of the porous body and the fiber diameter is measured in the same manner as mentioned above.

Thus, the fiber diameter so referred to herein means the mean fiber diameter value as measured in the manner mentioned above, and that mean value is required to be within the range mentioned above (3 to 40 µm).

In view of the retainability of the desired cells, the mesh opening of the material for separating stem cell is preferably not smaller in minor axis than 3 µm and not larger in major axis than 120 µm. When the minor axis is smaller than 3 µm, the efficiency in removing erythrocytes, leukocytes and platelets tends to lower and, further, clogging due to tissue-derived impurities, in particular fat droplets, tends to occur. When the major axis is larger than 120 µm, there is a tendency for the capture of the desired cells to become difficult. From the viewpoint of the efficiency in removing fat droplets, erythrocytes, leukocytes, platelets and the like, the mesh opening is more preferably 5 µm to 80 µm and, from the viewpoint of the efficiency in removing fat droplets, erythrocytes, leukocytes, platelets and the like and of the rate of recovery of the desired cells, it is still more preferably 5 µm to 70 µm.

The major axis means the distance between the two remotest points on the circumference of each pore forming the material for separating stem cell, and the minor axis means the distance between the two nearest points in contact with the pore and forming a line segment passing through the middle point between the two points used for determining the major axis.

When the material for separating stem cell is constituted of fibers, the mesh opening of the material for separating stem cell can be determined by the following method, for instance. The material for separating stem cell is photographed using a scanning electron microscope, the major axes and minor axes of substantial pores formed by crossing two or more different fibers are measured at 50 or more points using an image analyzer, and the mean major axis and minor axis values are calculated. Thus, the mesh opening range indicates a range whose lower limit value is the mean minor axis value determined in the above manner and whose upper limit is the mean major axis value.

When the material for separating stem cell is a porous body or the like, the mesh opening is defined in terms of the mean values of major axis portions and minor axis portions of pores of the porous body, which are measured in the same manner as described above.

The material for separating stem cell is preferably one substantially allowing the passage of erythrocytes and leukocytes therethrough. By saying "substantially allowing the passage of erythrocytes and leukocytes therethrough" herein, it is meant that at least 80% of erythrocytes and at least 30% of leukocytes can pass through the material for separating stem cell. From the viewpoint of the performance characteristics of the material for separating stem cell, it is more preferred that at least 85% of erythrocytes and at least 45% of leukocytes can pass through the material and, still more preferably, at least 90% of erythrocytes and at least 60% of leukocytes can pass through the same.

For attaining further improvements in the performance characteristics of the material for separating stem cell, the material for separating stem cell may be subjected to hydrophilization treatment. The hydrophilization treatment can result in suppressed nonspecific capture of cells other than the necessary cells, uniform passage of the body fluid or biological tissue-derived treated fluid through the material for separating stem cell, improvements in performance characteristics, and improved rates of recovery of the necessary cells, for instance.

As the method of hydrophilization treatment, there may be mentioned, among others, the method involving adsorption of a water-soluble polyhydric alcohol, or a hydroxyl group-, cationic group- or anionic group-containing polymer or copolymer (e.g. a polymer or copolymer of hydroxyethyl methacrylate, dimethylaminoethyl methacrylate and/or the like); the method involving adsorption of a water-soluble polymer (e.g. polyethylene glycol, polyvinylpyrrolidone, poly(vinyl alcohol); the method comprising immobilizing a hydrophilic polymer on a hydrophobic membrane (e.g. the method involving chemical bonding of a hydrophilic monomer to the surface); the method comprising irradiating the material for separating stem cell with electron beams; the method comprising irradiating the material for separating stem cell in hydrous condition with radiations to crosslink and insolubilize a hydrophilic polymer; the method comprising subjecting the material for separating stem cell to heat treatment in dry condition to insolubilize and immobilize a hydrophilic polymer; the method comprising sulfonating the hydrophobic membrane surface; the method comprising forming a membrane from a mixture of a hydrophilic polymer and a hydrophobic polymer dope; the method comprising providing the membrane surface with hydrophilic groups by treatment with an aqueous alkali solution (e.g. NaOH, KOH); the method comprising immersing a hydrophobic porous membrane with an alcohol then treating the membrane with an aqueous solution of a water-soluble polymer and, after drying, insolubilizing the polymer by heat treatment or irradiation etc.; and the method involving adsorption of a substance having surfactant properties.

As the hydrophilic polymer, there may be mentioned, polyvinylpyrrolidone, poly(vinyl alcohol), poly(ethylene glycol), ethyl-vinyl alcohol copolymers, poly(hydroxyethyl methacrylate), polysaccharides (cellulose, chitin, chitosan, etc.) and water-soluble polyhydric alcohols, among others.

As the hydrophobic polymer, there may be mentioned polystyrene, poly(vinyl chloride), polyolefins (polyethylene, polypropylene, etc.), acrylics, polyurethanes, vinylon, nylons and polyesters, among others.

As the substance having surfactant properties, there may be mentioned nonionic surfactants, lecithins, polyoxyethylene-hardened castor oil, sodium edetate, sorbitan sesquioleate, D-sorbitol, dehydrocholic acid, glycerol, D-mannitol, tartaric acid, propylene glycol, Makrogol species, lanolin alcohol and methylcellulose, among others.

As the nonionic surfactant, there may be roughly mentioned two types: polyhydric alcohol fatty acid ester type ones and polyoxyethylene type ones. As the polyhydric alcohol fatty acid ester type surfactants, there may be mentioned stearic acid glycerol esters, sorbitan fatty acid esters and sorbitan acyl esters, among others. As the polyoxyethylene type surfactants, there may be mentioned polyoxyethylene alcohol ethers, polyoxyethylene acyl esters, polyoxyethylenesorbitan acyl esters, polyoxyethylenesorbitan monolaurate, polyoxyethylenesorbitan monopalmitate, polyoxyethylenesorbitan monostearate, polyoxyethylenesorbitan tristearate and polyoxyethylenesorbitan monooleate, among others.

These may be used singly or in combination.

For further raising the rate of adhesion of the desired cells to the material for separating stem cell, a cell-adhering protein or an antibody against a specific antigen expressed on the desired cells may be immobilized on the material for separating stem cell.

As the cell-adhering protein, there may be mentioned fibronectin, laminin, vitronectin, collagen and so forth.

The antibody includes, but is not limited to, antibodies against CD133, CD90, CD105, CD166 and CD140a.

As for the immobilization method, use may arbitrarily be made of such conventional protein immobilization methods as the cyanogens bromide activation method, acid azide derivative method, condensation reagent method, diazo method, alkylation method and crosslinking method.

As for the manner of use of the material for separating stem cell, the material for separating stem cell as such may be used as a separating material, without confining it in a container or the like, or the material for separating stem cell having an arbitrary size may be used in a condition contained in a container having an inlet and an outlet; from the practical viewpoint, the latter is preferred.

The material for separating stem cell may be used for body fluid treatment either in the form of a sheet or sheets cut to an appropriate size or in a rolled-up form.

Now, the filter for separating stem cell according to the invention is described.

The filter for separating stem cell according to the invention comprises a container having a fluid inlet port and a fluid outlet port and the above-mentioned material for separating stem cell contained therein.

On that occasion, the material for separating stein cell may be received in the container either without compression or in a compressed state.

The material for separating stem cell is not restricted in its shape and form provided that the above-mentioned requirement is satisfied.

As a typical preferred example of the filter for separating stem cell, there may be mentioned one obtained by confining the material for separating stem cell in the form of a nonwoven fabric, with a thickness of about 0.1 cm to 5 cm in a confined condition, in such a container for a filter for separating stem cell as mentioned below. In this case, the thickness of the material for separating stem cell (in the confined condition) is preferably 0.1 cm to 5 cm and, from the viewpoint of cell recovery rate and of the efficiency of removal of fat droplets, erythrocytes, leukocytes, platelets and the like, it is more preferably 0.15 cm to 4 cm, still more preferably 0.2 cm to 3 cm. In cases where the thickness of the material for separating stem cell is less than the thickness mentioned above, the thickness requirement may be satisfied by using the material for separating stem cell in a laminated form.

The material for separating stem cell may also be confined in a container for a filter for separating stem cell in a rolled-up form. In the case of using the material in a rolled-up form, the body fluid to be treated may be caused to flow either from the inside to the outside of the roll or from the outside to the inside of the roll for capturing the desired cells.

The container for the filter for separating stem cell is not particularly restricted in shape or form, size or material.

The container may have any arbitrary shape or form, for example the form of a sphere, container, cassette, bag, tube or column. As preferred specific examples, there may be mentioned transparent or semitransparent cylindrical containers having a capacity of about 0.1 to 400 ml and a diameter of about 0.1 to 15 cm; and square or rectangular columns the top and bottom of which are square or rectangular, with each side having a length of about 0.1 cm to 20 cm, and which have a thickness of about 0.1 cm to 5 cm. These examples are, however, by no means restrictive of the scope of the invention.

The container can be prepared using any structural material. As the structural material, there may specifically be mentioned inert polymers, biocompatible metals and alloys and glasses, among others.

As the inert polymers, there may be mentioned acrylonitrile-based polymers such as acrylonitrile-butadiene-styrene terpolymers; halogenated polymers such as polytetrafluoroethylene, polychlorotrifluoroethylene, tetrafluoroethylene-hexafluoropropylene copolymers and poly(vinyl chloride); polyamides, polyimides, polysulfones, polycarbonates, polyethylene, polypropylene, poly(vinyl chloride)-acrylic copolymers, polycarbonate-acrylonitrile-butadiene-styrene, polystyrene and polymethylpentene, among others. As metallic materials (biocompatible metals and alloys) useful as container materials, there may be mentioned stainless steel, titanium, platinum, tantalum, gold, and alloys thereof as well as gold-plated alloy iron species, platinum-plated alloy iron species, cobalt-chromium alloys and titanium nitride-coated stainless steel species, among others.

Particularly preferred are sterilization-resistant materials, specifically polypropylene, poly(vinyl chloride), polyethylene, polyimides, polycarbonates, polysulfones, polymethylpentene and the like.

A method of using the filter for separating stem cell is roughly described below.

First, a body fluid or biological tissue-derived treated fluid is allowed to flow into the filter for separating stem cell from the fluid inlet side. Unnecessary cells and unnecessary substances, such as fat droplets, erythrocytes, leukocytes, platelets and the enzyme or enzymes used, flow out from the fluid outlet side substantially without being captured and, thus, the desired cells can be captured within the material for separating stem cell. Then, a washing fluid is passed through the filter in the same direction, whereby the residual unnecessary cells and unnecessary substances, such as fat droplets, erythrocytes, leukocytes, platelets and the enzyme or enzymes used, as remaining in the material for separating stem cell can be mostly washed out and removed. Further, a cell recovering fluid is caused to flow from the fluid outlet side in the direction opposite to the direction of the flow of the body fluid or biological tissue-derived treated fluid and the washing fluid, whereby the desired cells can be separated and recovered with high efficiency.

While the filter for separating stem cell comprises a container having an inlet and an outlet for a body fluid or a biological tissue-derived treated fluid and the material for separating stem cell contained therein, a preferred one comprises a container further having an inlet and an outlet for the cell washing fluid and/or the cell recovering fluid or, further, a container equipped with a culture bag for culturing the recovered cells as such, and the material for separating stem cell contained therein.

More specifically, the filter for separating stem cell is preferably equipped with a fluid inlet port for feeding a body fluid or a biological tissue-derived treated fluid, and a fluid outlet port for discharging the body fluid or biological tissue-derived treated fluid that has passed through the material for separating stem cell and, further with a washing fluid inlet port for washing out the unnecessary cells and unnecessary substances remaining in the material for separating stem cell either at the fluid inlet port or independently at a site other than the fluid inlet port on the fluid inlet port side and with a cell recovery fluid inlet port for recovering the cells captured by the material for separating stem cell (for causing the cell recovering fluid to flow in the direction opposite to the direction of the flow of the body fluid or biological tissue-derived treated fluid and the washing fluid) at the fluid outlet port or independently at a site other than the fluid outlet port on the fluid outlet port side.

Preferably, the filter for separating stem cell is further provided with a bag for receiving the cell recovering fluid containing the cells captured by the material for separating stem cell at the fluid inlet port or washing fluid inlet port or at a site other than the fluid inlet port and washing fluid inlet port on the fluid inlet side.

Further, the bag for receiving the cell recovering fluid containing the cells captured by the material for separating stem cell is preferably a bag allowing cell culture therein.

Thus, the filter for separating stem cell may be equipped with a culture bag for culturing the cells recovered. The culture bag can be provided at the fluid inlet port or washing fluid inlet port or independently on the fluid inlet side so that the cell recovering fluid containing the cells captured by the material for separating stem cell may be recovered in a closed system. After recovery of the cell suspension, the bag may be separated from the filter for separating stem cell for cell culture.

The bag material is preferably a material high in oxygen permeability and high in cell adhesion level. As the material high in oxygen permeability, there may be mentioned polymethylpentene, cyclic polyolefins, olefinic thermoplastic elastomers, styrenic thermoplastic elastomers and polyamide type thermoplastic elastomers, among others. As the material high in cell adhesion level, there may be mentioned polystyrene, polypropylene and poly(vinyl chloride), among others. A bag high in oxygen permeability can be rendered adhesive to cells, for example, by fixing a material high in cell adhesion level to the bag while maintaining the high oxygen permeability. Such mode of embodiment is, however, by no means limitative of the scope of the invention.

The bag may be in the form of a blood bag in common use or may be in the form of a flat cartridge, for instance.

The method of separating and recovering stem cells according to the invention is a method of separating and recovering stem cells from a body fluid or biological tissue-derived treated fluid using the above material for separating stem cell or filter for separating stem cell.

The stem cells can be separated by capturing the stem cells from the body fluid or biological tissue-derived treated fluid by the above-mentioned material for separating stem cell or filter for separating stem cell.

The method of recovering stem cells according to the invention is characterized in that the body fluid or biological tissue-derived treated fluid is introduced into the filter for separating stem cell from the fluid inlet side thereof and, after washing by causing a washing fluid to flow from the fluid inlet side, a cell recovering fluid is caused to flow from the fluid outlet side to thereby recover the stem cells captured by the material for separating stem cell.

The stem cell recovering method is described below. The fluid to be fed may be any of the body fluids and biological tissue-derived treated fluids mentioned above. In the following description, however, a body fluid is taken by way of example.

1) Body Fluid Feeding Step;

On the occasion of feeding a body fluid to the filter for separating stem cell from the fluid inlet side, the body fluid may be fed to the filter from a container containing the body fluid through a fluid feeding circuit either in the manner of free fall or by means of a pump. It is also possible to connect a syringe containing the body fluid to the filter and inject the body fluid directly into the filter by manually operating the syringe. In the case of pump feeding, the rate of flow is, but is not limited to, about 0.1 ml/min to 100 ml/min.

2) Cell Washing Step;

On the occasion of feeding a washing fluid to the filter for separating stem cell from the fluid inlet side, the washing fluid may be fed through the circuit to the filter either in the manner of free fall or by means of a pump. In the case of pump feeding, the rate of flow may be about 0.1 ml/min to 100 ml/min. The volume of the washing fluid is preferably about 1 to 100 times the volume of the capacity of the filter for separating stem cell, although it may depend on the capacity of the filter for separating stem cell.

As the cell washing fluid, there may be mentioned physiological saline, Ringer solution, cell culture media, phosphate buffer solutions and like ordinary buffer solutions.

From the safety viewpoint, however, physiological saline is preferred.

3) Cell Recovery Step;

A cell recovering fluid is introduced into the filter for separating stem cell in the direction opposite to the direction of the flow of the body fluid and washing fluid (i.e. from the fluid outlet side) to thereby recover stem cells.

The recovery of stem cells by injecting the cell recovering fluid into the filter for separating stem cell can be realized, for example, by vigorously pushing, manually or by other means, the plunger of a syringe or the like containing the cell recovering fluid sucked up therein in advance. While the amount of the recovering fluid and the rate of flow may vary depending on the filter capacity, the cell recovering fluid is preferably injected into the filter in an amount about 1 to 100 times the filter capacity at a flow rate of about 0.5 ml/sec to 20 ml/sec, although these values have no restrictive meaning.

The cell recovering fluid is not particularly restricted provided that it is isotonic. Thus, it includes those in actual use in injectable solutions, for example physiological saline and Ringer solution, as well as buffer solutions and cell culture media, among others.

For raising the rate of recovery of the stem cells captured by the filter for separating stem cell, the viscosity or consistency of the cell recovering fluid may be increased. The substance to be added to the cell recovering fluid for that purpose includes, but is not limited to, albumin, fibrinogen, globulin, dextran, hydroxyethylstarch, hydroxyethylcellulose, collagen, hyaluronic acid and gelatin.

In cases where the stem cells recovered in the bag are to be amplified, there may be mentioned, for example, the method comprising using, as the cell recovering fluid, a culture medium (e.g. Dulbecco MEM (Nissui), α-MEM (Gibco BRL), MEM (Nissui), IMEM (Nissui), RPMI-1640 (Nissui)) and, as the filter, a culture bag with a filter attached and recovering the cells directly in such bag. An amount of about 5 to 20% of serum may be added according to need.

In cases where the cells recovered are injected into a patient's affected part, for instance, without passing any culture step, a cell recovering fluid whose safety has been established, for example an isotonic solution, such as physiological saline, which is commonly used in instillation, is preferably used.

Then, after stem cell recovery in a bag, a necessary amount of a culture medium is added to the bag according to need and the bag is detached from the filter and, as such, submitted to cultivation.

The conditions in culturing the stem cells recovered in the bag as such are not particularly restricted but the cells are desirably cultured in a $CO_2$ incubator at 37° C. for 7 to 14 days using, as the medium, α-MEM (Gibco BRL) supplemented with 15 to 20% of fetal bovine serum, for instance.

Thereafter, passages may be carried out for increasing the number of cells. In this case, the stem cells can be detached and recovered from the culture dish or the like using a chelating agent or a cell detaching agent such as dispase or collagenase, preferably trypsin.

As for the medium exchange, the old medium may be sucked off, followed by addition of an equal amount of the fresh medium, or an appropriate amount of the fresh medium may be added without sucking off the old medium. In the case of bag culture, in particular, the addition of fresh portions of the medium makes it possible to carry out the series of steps from stem cell separation to amplification in a closed system and thus prevent contamination and bring about marked improvements in operation efficiency.

In the culture mentioned above, the stem cells can be differentiated into various cells by adding a differentiation inducer. The differentiation inducer is not particularly restricted but includes inducers of differentiation into cartilage, such as dexamethasone, TGF-β, insulin, transferrin, ethanolamine, proline, ascorbic acid, piruvate salts and selenium; inducers of differentiation into bone, such as dexamethasone, β-glycerophosphate, vitamin C and ascorbate salts; inducers of differentiation into cardiac muscle, such as EGF, PDGF and 5-azacytidine; inducers of differentiation into nerve, such as EGF, bFGF and bHLH; and inducers of differentiation into blood vessel, such as bFGF and VEGF.

The method of producing a multipotent cell fraction according to the invention is characterized in that the stem cells recovered by the above-mentioned method of recovering stem cells are further amplified. More specifically, the method is characterized in that it comprises the following steps (a) to (c).

(a) The step of treating a body fluid using the above-mentioned filter for separating stem cell;
(b) The step of recovering the cell fraction captured in the filter for separating stem cell; and
(c) The step of amplifying the stem cells recovered.

The method of amplification is not particularly restricted but, for example, there may be mentioned the method comprising using, as the cell recovering fluid, a culture medium (e.g. Dulbecco MEM (Nissui), α-MEM (Gibco BRL), MEM (Nissui), IMEM (Nissui), RPMI-1640 (Nissui)), recovering the cells directly in a culture bag with a filter attached and carrying out the amplification in a 5% $CO_2$ incubator at 37° C. An amount of about 5 to 20% of serum may be added to this culture medium according to need.

In each of the methods mentioned above, the body fluid and biological tissue is preferably of the mammalian origin.

Thus, the body fluid and biological tissue can be obtained from a target mammal. The mammal is not particularly restricted but includes, among others, humans, monkeys, dogs, cats, swine, cattle and horses.

The stem cells obtained by the above-mentioned method of recovering stem cells also fall within the scope of the present invention. The stem cells are multipotent.

In the practice of the invention, the stem cells obtained by using the above-mentioned material for separating stem cell or filter for separating stem cell may be offered or used in the form of undifferentiated cells either after amplification or without amplification. They may also be used, after differentiation induction by means of such a differentiation inducer as mentioned above, for instance, as cells to be transplanted into patients with a cartilage lesion, cells to be transplanted into patients with a bone disease, cells to be transplanted into patients with a myocardial disease or vascular disease, or cells to be transplanted into patients with an injured nerve tissue. These do not make up a limitative list, however.

In the practice of the present invention, the stem cells obtained by using the above-mentioned material for separating stem cell or filter for separating stem cell can be used as cells for therapeutic purposes.

Further, the cells for therapeutic purposes can be applied to the treatment of various diseases or to tissue enlargement techniques. A list of specific targets of treatment includes, but is not limited to, such disease as stem cell exhaustion diseases, bone diseases, cartilage diseases, ischemic diseases, vascular diseases, neuropathy, burns, chronic inflammation, cardiac failure, immunodeficiency and Crohn's disease; and such tissue enlargement treatments as breast enlargement, wrinkle removal, cosmetic surgery and treatment of tissue depression.

Effect of the Invention

By using the material for separating stem cell and filter for separating stem cell according to the invention, it becomes possible to separate and recover adherent stem cells capable of differentiating into various cells or organs, in a condition almost free of erythrocytes, leukocytes and platelets, in a simple and easy manner from such a body fluid as bone marrow fluid, peripheral blood or umbilical cord blood. Further, by using the material for separating stem cell and filter for separating stem cell according to the invention, it becomes possible to separate and recover biological tissue-derived stem cells capable of differentiating into various cells or organs, in a condition substantially free of tissue-derived impurities such as fat droplets, erythrocytes, leukocytes and platelets and of the enzyme or enzymes used for disintegration, among others, in a simple and easy manner from a biological tissue-derived treated fluid. Furthermore, the adherent stem cells and biological tissue-derived stem cells obtained by using the material for separating stem cell and filter for separating stem cell are useful as therapeutic cells for use in revascularization, tissue enlargement and like regenerative medicine and cellular medicine techniques.

Further, the stem cells recovered by the separation method using a filter for separating stem cell containing the material for separating stem cell according to the invention as packed therein can be used as such or can be amplified in a closed system and, therefore, such filter can be provided as a filter for preparing therapeutic cells for use in regenerative medicine or cellular medicine, for example in heart muscle regeneration or revascularization. Furthermore, by using the filter for separating stem cell, it becomes possible to provide stem cells very useful as a cell source for regenerative medicine and hardly causative of adverse reactions, with a very low percentage of coexisting fat droplets, erythrocytes, leukocytes, platelets and other contaminants. By integrating a culture bag with the filter for separating stem cell, highly safe stem cells for therapeutic uses can be prepared in a closed system encompassing cell collection to amplification.

BEST MODES FOR CARRYING OUT THE INVENTION

The following examples illustrate the invention in detail. These examples are, however, by no means limitative of the scope of the invention.

The density K (basis weight $(g/m^2)$/thickness (m)), fiber diameter and mesh opening of each material for separating stem cell were determined as described hereinabove.

[Example 1] Separation of Adherent Stem Cells from Bone Marrow Fluid Using a Filter for Separating Stem Cell (1) Cell Source A domestic pig weighing about 30 kg was anesthetized by intramuscular injection of Ketalar and Selactar, followed by additional intravenous injection of Nembutal. Bone marrow fluid was collected from the iliac bone into a 10-ml syringe containing heparin added in advance in an amount to make about 20 IU/ml using a 15 G puncture needle. Then, heparin was added to the bone marrow pool thus collected to a final concentration of 50 IU/ml, followed by thorough mixed up by repeated reversal.

(2) Preparation of a Filter for Separating Stem Cell

A filter for separating stem cell was prepared by putting together twelve piled-up split fiber nonwoven fabrics made of polyester and polypropylene [density K (basis weight $(g/m^2)$/thickness (m)=$1.3 \times 10^5$ ($73/(5.5 \times 10^{-4})$), fiber diameter=8±5 µm (i.e. mean value=8 µm; hereinafter the same shall apply), mesh opening=5 to 50 µm (minor axis-major axis; hereinafter the same shall apply)) from top to bottom by means of a stopper with an outside diameter of 1 cm, an inside diameter of 7 mm and a height of 5 mm and inserting the pile, as a material for separating stem cell, into a cylindrical polypropylene tube having an inside diameter of 1 cm and equipped with an inlet and an outlet for fixation of the material for separating stem cell.

(3) Cell Separation Performance Evaluation

The nonwoven fabric pile was washed with physiological saline in an amount about 6 times the volume of the filter for separating stem cell. Then, 2 ml of the bone marrow fluid was passed through the filter at a flow rate of 0.5 ml/min using a syringe pump, and the number of cells on the filter outlet side was checked using an automated blood cell counter (Sysmex K-4500). Then, 2 ml of physiological saline was passed through the filter in the same direction at the same flow rate to thereby wash away erythrocytes, leukocytes and platelets. Thereafter, 2 ml of a cell culture medium (α-MEM) containing 15% of fetal bovine serum was caused to flow swiftly in the direction reverse to the direction of the flow of the bone marrow fluid to thereby recover the desired cell fraction, and the number of cells in the solution recovered was checked using an automated blood cell counter (Sysmex K-4500). The percent passage for each cell species was calculated by dividing the number of cells after passage through the filter by the number of cells before passage through the filter. The recovery rate for each cell species was calculated by dividing the number of cells in the recovered fluid by the number of cells before passage through the filter. As a result, the percent passages of erythrocytes and platelets were not lower than 95% and the percent passage of leukocytes was about 75%. The recovery rates were 0.5% for erythrocytes, about 3% for platelets, and about 20% for leukocytes. These data indicate that the filter for separating stem cell can remove most of erythrocytes and platelets and at least 80% of leukocytes.

Then, 5 ml of a cell culture medium (α-MEM) containing 15% of fetal bovine serum was added to 2 ml of the cell suspension recovered, the whole was transferred to a polystyrene dish (35 mm in diameter) and the cells were cultured in a $CO_2$ incubator at 37° C. Medium exchange was carried out at intervals of 2 to 3 days and, after 9 days from the start of cultivation, the colonies that had appeared were stained with crystal violet and then counted. As a result, the number of colonies that had appeared was 33/dish.

Then, the cells obtained by 10 days of cultivation of the cells recovered by the filter for separating stem cell were subjected to cartilage formation evaluation. The cells obtained by cultivating and amplifying the cells separated and recovered by the above method were washed once with 20 ml of DMEM high glucose medium (product of Gibco BRL) and then recovered by centrifugation (1,000 rpm, 10 min, 4° C.). They were again suspended, to a cell concentration of $4 \times 10^5$ cells/ml, in Gibco BRL DMEM high glucose medium supplemented with additives promoting the induction of differentiation into cartilage (TGF-β3 human recombinant, final concentration 10 ng/ml, Funakoshi; dexamethasone, final concentration 100 nM, Sigma; ascorbic acid phosphate, final concentration 50 µg/ml, Wako; sodium pyruvate, final concentration 100 µg/ml; L-proline, final concentration 40 µg/ml, Cosmo Bio; ITS Plus (insulin, transferrin, selenium, bovine serum albumin), the commercial stock solution added in an amount of 1/100 of the medium). A 0.5-ml portion of this cell suspension was transferred to a 15-ml Falcon tube. Then, centrifugation (1,000 rpm, 10 min, 4° C.) was carried out, whereupon the cells became a pellet-like matter. In that condition, the stopper of the tube was loosened and the cells were cultured in a 5% $CO_2$ incubator at 37° C. for 3 weeks, during which medium exchange was carried out twice per week. After completion of the cultivation, the spherical cell mass was recovered, fixed with formalin for tissue fixation and stained with the cartilage matrix staining agent toluidine blue. As a result of tissue slice observation under a microscope, metachromasy, namely violet staining of the matrix of cartilage, was observed.

Further, using the cells obtained by amplification, by the same method as mentioned above, of the cells separated by the filter for separating stem cell, a bone tissue generation test was carried out. The mesenchymal stem cells obtained by cultivation were suspended in Gibco BRL α-MEM+15% fetal bovine serum to a final concentration of $1 \times 10^4$ cells/ml, and the suspension was sowed onto a 12-well culture plate (distributed in 2-ml portions into wells; $2 \times 10^4$ cells/well). After the lapse of 24 hours, three additives promoting the differentiation into bone (β-glycerophosphate, Calbiochem 35675; ascorbic acid phosphate, Wako 013-12061; dexamethasone, Sigma A D 8893) were added to the respective concentrations of 10 mM, 50 FL g/ml and 100 nM to give an induced bone differentiation group. In a non-induced group, β-glycerophosphate alone was added. In these groups, the cells were cultured in an incubator in the presence of 5% $CO_2$ at 37° C. for 2 weeks. Whole amount (2 ml) medium exchange was carried out three times a week. On the day of final medium exchange (2 days before the day of analysis), Calcein (Dojin 344-00431) was added to a concentration of 1 FL g/ml and the culture was continued. On the day of analysis, the extent of ossification in each well was evaluated based on the amount of calcium deposited. More specifically, the extent of ossification can be determined by measuring the fluorescence intensity of Calcein bound to calcium. Thus, the fluorescence intensity per unit area (volume/area) was measured using the fluorescence scanner Typhoon 8600 (product of Amersham Pharmacia). As a result, the calcium deposit index fluorescence intensity (volume/area) was 4,080.

Example 2

Following the procedure of Example 1 in the same manner except that the filter for separating stem cell used contained nonwoven fabrics made of rayon and polyolefin [density K (basis weight $(g/m^2)$/thickness (m)=$2.0 \times 10^5$ ($110/(5.5 \times 10^{-4})$), fiber diameter=15±9 μm, mesh opening=5 to 48 μm) as the material for separating stem cell, the percent cell passages, the recovery rates and the number of colonies that had appeared were determined, a metachromasy observation was made and the Calcein fluorescence intensity was measured. As a result, the percent passages of erythrocytes and platelets were each about 95% and the percent passage of leukocytes was about 78%. The recovery rates were 0.3% for erythrocytes and about 4% for platelets, indicating that most of erythrocytes and platelets can be removed by the filter for separating stem cell used. The leukocyte recovery rate was about 16%, indicating that 80% or more of leukocytes can be removed. The number of colonies that had appeared was 48/dish. It was observed that the cell mass obtained by cell amplification showed metachromasy, namely violet staining of the matrix of cartilage. Further, the fluorescence intensity (volume/area) indicative of the amount of calcium deposited was 4,700.

Example 3

Following the procedure of Example 1 in the same manner except that the filter for separating stem cell used contained nonwoven fabrics made of polyester [density K (basis weight $(g/m^2)$/thickness (m)=$5.0 \times 10^5$ ($250/(5.5 \times 10^{-4})$), fiber diameter=18±11 μm, mesh opening=8 to 43 μm) as the material for separating stem cell, the percent cell passages, the recovery rates and the number of colonies that had appeared were determined, a metachromasy observation was made and the Calcein fluorescence intensity was measured. As a result, the percent passages were about 93% for erythrocytes, about 79% for platelets and about 81% for leukocytes. The recovery rates were 0.4% for erythrocytes and about 8% for platelets, indicating that most of erythrocytes and platelets can be removed by the filter for separating stem cell used. The leukocyte recovery rate was about 8%, indicating that 90% or more of leukocytes can be removed. The number of colonies that had appeared was 33/dish. It was observed that the cell mass obtained by cell amplification showed metachromasy, namely violet staining of the matrix of cartilage. Further, the fluorescence intensity (volume/area) indicative of the amount of calcium deposited was 4,320.

Example 4

Following the procedure of Example 1 in the same manner except that the filter for separating stem cell used contained nonwoven fabrics made of polyester [density K (basis weight $(g/m^2)$/thickness (m)=$5.9 \times 10^4$ ($200/(3.4 \times 10^{-3})$), fiber diameter=14±8 μm, mesh opening=7 to 100 μm) as the material for separating stem cell, the percent cell passages, the recovery rates and the number of colonies that had appeared were determined, a metachromasy observation was made and the Calcein fluorescence intensity was measured. As a result, the percent passages were about 96% for erythrocytes, about 78% for platelets and about 86% for leukocytes. The recovery rates were 1% for erythrocytes and about 10% for platelets, indicating that most of erythrocytes and platelets can be removed by the filter for separating stem cell used. The leukocyte recovery rate was about 9%, indicating that 90% or more of leukocytes can be removed. The number of colonies that had appeared was 34/dish. It was observed that the cell mass obtained by cell amplification showed metachromasy, namely violet staining of the matrix of cartilage. Further, the fluorescence intensity (volume/area) indicative of the amount of calcium deposited was 4,510.

Example 5

Following the procedure of Example 1 in the same manner except that the filter for separating stem cell used contained nonwoven fabrics made of polyester [density K (basis weight $(g/m^2)$/thickness (m)=$1.2 \times 10^5$ ($85/(7.0 \times 10^{-4})$), fiber diameter=11±4 μm, mesh opening=5 to 52 μm) as the material for separating stem cell, the percent cell passages, the recovery rates and the number of colonies that had appeared were determined, a metachromasy observation was made and the Calcein fluorescence intensity was measured. As a result, the percent passages of erythrocytes and platelets were each about 95%, and the percent passage of leukocytes was about 90%. The recovery rates were 1% for erythrocytes and about 5% for platelets, indicating that most of erythrocytes and platelets can be removed by the filter for separating stem cell used. The leukocyte recovery rate was about 7%, indicating that 90% or more of leukocytes can be removed. The number of colonies that had appeared was 31/dish. It was observed that the cell mass obtained by cell amplification showed metachromasy, namely violet staining of the matrix of cartilage. Further, the fluorescence intensity (volume/area) indicative of the amount of calcium deposited was 3,740.

Reference Example 1

The procedure of Example 1 was followed in the same manner except that the addition of the above-mentioned factors inducing the differentiation into cartilage to the medium was omitted, and the cartilage matrix formation performance was evaluated. As a result, metachromasy, namely violet staining of the matrix of cartilage, was not observed.

Reference Example 2

The procedure of Example 1 was followed in the same manner except that the addition of the above-mentioned bone tissue formation factors to the medium was omitted, and the bone tissue formation performance was evaluated. As a result, the fluorescence intensity (volume/area) indicative of the amount of calcium deposited was 250.

Comparative Example 1

Following the procedure of Example 1 in the same manner except that the filter for separating stem cell used contained nonwoven fabrics made of polypropylene [density K (basis weight $(g/m^2)$/thickness (m)=$1.1\times10^6$ (1100/($1.0\times10^{-3}$)), fiber diameter=$8\pm3$ μm, mesh opening=3 to 20 μm) as the material for separating stem cell, the percent cell passages, the recovery rates and the number of colonies that had appeared were determined. As a result, the percent passages were about 80% for erythrocytes, about 1% for platelets and about 1% for leukocytes. The recovery rate for erythrocytes was about 10%, while neither platelets nor leukocytes could be recovered. The number of colonies that had appeared was 0/flask.

Comparative Example 2

Following the procedure of Example 1 in the same manner except that the filter for separating stem cell used contained nonwoven fabrics made of cotton [density K (basis weight $(g/m^2)$/thickness (m)=$8.3\times10^3$ (25/($3.0\times10^{-3}$)), fiber diameter=$11\pm4$ μm, mesh opening=3 to 25 μm) as the material for separating stem cell, the percent cell passages, the recovery rates and the number of colonies that had appeared were determined. As a result, the percent passages were about 99% for erythrocytes, about 99% for platelets and about 96% for leukocytes. The recovery rates were 0.3% for erythrocytes, 0.1% for platelets and about 1% for leukocytes. The number of colonies that had appeared was 0/flask.

Comparative Example 3

A 2-ml portion of the bone marrow fluid collected in the same manner as in Example 1 was mixed with 2 ml of phosphate buffer PBS(−) two-fold dilution). Then, 3 ml of Ficoll Paque plus (Amersham) was added to a 15-ml centrifuge tube, and the diluted bone marrow fluid (4 ml) prepared in advance was layered on that solution. Centrifugation was carried out at 1,400 rpm and at room temperature for 30 minutes and the resulting monocyte fraction layer was recovered. About 10 ml of PBS(−) was added thereto and the cells were washed at 1,300 rpm for 5 minutes. Then, similarly, about 10 ml PBS(−) was added and the cells were washed again at 1,200 rpm for 5 minutes. The rewashed cells were suspended in 2 ml of PBS(−), and the respective cell counts were determined using the automated blood cell counter mentioned above and the cell recovery rates were calculated. The number of colonies that had appeared was determined, a metachromasy observation was made and the Calcein fluorescence intensity was determined in the same manner as in Example 1. As a result, the erythrocyte recovery rate was 1%, the platelet recovery rate was 11% and the leukocyte recovery rate was 83%. The number of colonies that had appeared was 46/dish. Metachromasy, namely violet staining of the matrix of cartilage, was observed in the cell mass resulting from cell amplification. Further, the fluorescence intensity (volume/area) indicative of the amount of calcium deposited was 4,210.

Comparative Example 4

A 2-ml portion of the bone marrow fluid collected in the same manner as in Example 1 was mixed up with 2 ml of PBS(−). To this starting bone marrow fluid (4 ml) for erythrocyte sedimentation was added a 1/5 amount of HES (product of Nipro, a 6% aqueous solution of hydroxyethyl-starch, molecular weight 400,000) to give a final concentration of 1%. Five minutes of centrifugation at 530 rpm (50 g) gave two layers (relatively clear upper layer and lower erythrocyte layer) and the uppermost layer (transparent layer alone) was recovered. Thereto was added about 10 ml of PBS(−), and the cells were washed at 1,300 rpm for 5 minutes. The cells were then resuspended in 2 ml of PBS(−), and the respective cell counts were determined using the automated blood cell counter mentioned above and the cell recovery rates were calculated. Further, the number of colonies that had appeared was determined in the same manner as in Example 1. As a result, the erythrocyte recovery rate was 6%, the platelet recovery rate was 51% and the leukocyte recovery rate was 74%. The number of colonies that had appeared was 29/dish.

The percent erythrocyte, platelet and leukocyte passage data obtained in Examples 1 to 5 and Comparative Examples 1 and 2 are summarized in Table 1. The erythrocyte, platelet and leukocyte recovery rates obtained in Examples 1 to 5 and Comparative Examples 1 to 4 are summarized in Table 2. The colony counts obtained in Examples 1 to 5 and Comparative Examples 1 to 4 are summarized in Table 3. The bone tissue formation evaluation results obtained in Examples 1 to 5, Comparative Example 3 and Reference Example 2 are summarized in Table 4. The cartilage formation evaluation results (namely the results of staining with the cartilage matrix staining agent (toluidine blue)) obtained in Examples 1 to 5, Comparative Example 3 and Reference Example 1 are shown in FIG. 1.

TABLE 1

Respective cell species passage rates

Unit: %

| Original bone marrow | Leukocyte | | Erythrocyte | | Platelet | |
| --- | --- | --- | --- | --- | --- | --- |
| | Mean | ±SD | Mean | ±SD | Mean | ±SD |
| Example 1 | 76.1 | 0.5 | 96.3 | 1.2 | 96.4 | 17.3 |
| Example 2 | 78.4 | 0.3 | 95.2 | 1.2 | 94.8 | 5.9 |
| Example 3 | 81.1 | 9.5 | 92.8 | 0.8 | 78.6 | 17.1 |
| Example 4 | 85.5 | 3.0 | 95.5 | 0.7 | 77.8 | 16.3 |
| Example 5 | 89.9 | 0.6 | 95.4 | 1.5 | 94.5 | 14.4 |
| Comp. Ex. 1 | 1.2 | 0.3 | 81.3 | 1.3 | 1.3 | 0.7 |
| Comp. Ex. 2 | 96.4 | 4.7 | 98.7 | 1.1 | 99.1 | 5.3 |

TABLE 2

Respective cell species recovery rates

Unit: %

| Original bone marrow | Leukocyte | | Erythrocyte | | Platelet | |
| --- | --- | --- | --- | --- | --- | --- |
| | Mean | ±SD | Mean | ±SD | Mean | ±SD |
| Example 1 | 19.5 | 0.0 | 0.5 | 0.1 | 3.1 | 0.9 |
| Example 2 | 16.3 | 0.6 | 0.3 | 0.1 | 3.5 | 0.9 |
| Example 3 | 7.8 | 1.3 | 0.4 | 0.1 | 7.6 | 3.9 |
| Example 4 | 9.1 | 2.0 | 1.0 | 0.2 | 9.8 | 1.7 |
| Example 5 | 7.2 | 0.7 | 1.1 | 0.4 | 4.6 | 3.9 |
| Comp. Ex. 1 | 0.0 | 0.0 | 10.4 | 3.4 | 0.0 | 0.0 |
| Comp. Ex. 2 | 1.0 | 0.3 | 0.3 | 0.2 | 0.1 | 0.1 |
| Comp. Ex. 3 | 83.0 | 4.3 | 1.0 | 0.3 | 11.0 | 0.4 |
| Comp. Ex. 4 | 74.0 | 15.1 | 6.0 | 5.7 | 51.0 | 17.8 |

TABLE 3

Colony counts

|  | Number of colonies | Unit: colonies/dish ±SD |
|---|---|---|
| Example 1 | 33 | 4 |
| Example 2 | 48 | 3 |
| Example 3 | 33 | 8 |
| Example 4 | 34 | 9 |
| Example 5 | 31 | 4 |
| Comp. Ex. 1 | 0 | 0 |
| Comp. Ex. 2 | 0 | 0 |
| Comp. Ex. 3 | 46 | 4 |
| Comp. Ex. 4 | 29 | 4 |

TABLE 4

Fluorescence intensities (indicative of amount of calcium deposited)

|  | Fluorescence intensity |
|---|---|
| Example 1 | 4080 |
| Example 2 | 4700 |
| Example 3 | 4320 |
| Example 4 | 4510 |
| Example 5 | 3740 |
| Comp. Ex. 3 | 4210 |
| Ref. Ex. 2 | 250 |

From the results shown above, it was revealed that the filters for separating stem cell in which the respective materials for separating stem cell according to the invention are used can give adherent cell recovery rates comparable to the recovery rate attainable by the Ficoll method which is currently a standard method for stem cell recovery. It was also shown that when the cells recovered are amplified and induced to differentiate into cartilage or bone, the same levels of cartilage matrix or bone tissue formation as attainable by using the Ficoll method can be attained. It is thus evident that by using the filters for separating stem cell in which the present materials for separating stem cell are used, it has become possible to markedly prevent erythrocytes, leukocytes and platelets, among others, from mixing in and separate and recover, in a simple and easy manner and selectively, adherent stem cells capable of differentiating. It is further evident that the present filters for separating stem cell make it possible to carry out the series of treatments from separation and recovery of adherent stem cells from a body fluid to amplification of the cells in a closed system and therefore are filters useful from the contamination prevention viewpoint as well.

Example 6

Following the procedure of Example 1 in the same manner except that the filter for separating stem cell used contained nonwoven fabrics made of rayon and polyester [density K (basis weight $(g/m^2)$/thickness (m)=$1.8\times10^5$ ($95/(5.2\times10^{-4})$), fiber diameter=$15\pm10$ μm, mesh opening=5 to 50 μm) as the material for separating stem cell, the percent cell passages, the recovery rates and the number of colonies that had appeared were determined, a metachromasy observation was made and the Calcein fluorescence intensity was measured. As a result, the percent passages were about 96% for erythrocytes, about 73% for platelets and about 84% for leukocytes. The recovery rates were 0.2% for erythrocytes, about 5% for platelets, indicating that most of erythrocytes and platelets could be removed by the filter for separating stem cell. The leukocyte recovery rate was about 15%, indicating that 80% or more of leukocytes can be removed. The number of colonies that had appeared was 50/dish. It was observed that the cell mass obtained by cell amplification showed metachromasy, namely violet staining of the matrix of cartilage. Further, the fluorescence intensity (volume/area) indicative of the amount of calcium deposited was 4,680.

Comparative Example 5

Following the procedure of Example 1 in the same manner except that the filter for separating stem cell used contained nonwoven fabrics made of polyester [density K (basis weight $(g/m^2)$/thickness (m)=$2.0\times10^5$ ($60/(3.0\times10^{-4})$), fiber diameter=2.3 μm, mesh opening=3 to 20 μm) as the material for separating stem cell, the percent cell passages, the recovery rates and the number of colonies that had appeared were determined. As a result, the percent passages were about 75% for erythrocytes, about 15% for platelets and about 10% for leukocytes. The recovery rates were about 75% for leukocytes, about 15% for erythrocytes and about 5% for platelets. The number of colonies that had appeared was 6/dish. Thus, 70% or more of leukocytes were captured and the colony count was not so high, hence the results cannot be said to be such that selective capture of stem cells was attained.

[Example 7] Separation of Biological Tissue-Derived Stem Cells from Subcutaneous Fat Using a Material for Separating Stem Cell (1) Preparation of a Treated Fluid by Enzymatic Disintegration of a Subcutaneous Adipocyte Tissue A rabbit (Japanese albino) weighing 3.5 kg was euthanized by excess administration of Ketalar/Selactar, and 50 g of dorsal subcutaneous fat was collected (FIG. 2). This white fat was minced with surgical scissors and then shaken with 100 mL of 0.075% (w/v) collagenase/phosphate buffered saline (pH=7.4) at 37° C. (1 hour). This procedure disintegrated the subcutaneous fat and made the same a viscous fluid having fluidity. This enzyme-treated fluid was allowed to stand while maintaining the temperature at 37° C. to separate into two layers (FIG. 3; upper layer: fat layer, lower layer: aqueous solution layer), and the lower aqueous solution layer (enzyme-treated fluid) was recovered.

(2) Preparation of a Filter for Separating Stem Cell

A filter for separating stem cell was prepared by putting together twelve piled-up split fiber nonwoven fabrics made of polyester and polypropylene [density K (basis weight $(g/m^2)$/thickness (m)=$1.1\times10^5$ ($73/(6.7\times10^{-4})$), fiber diameter=$8\pm5$ μm, mesh opening=5 to 50 μm) from top to bottom by means of a stopper with an outside diameter of 12 mm, an inside diameter of 7 mm and a height of 5 mm and inserting the pile, as a material for separating stem cell, into a cylindrical tube having an inside diameter of 12 mm and equipped with an inlet and an outlet for fixation of the material for separating stem cell.

(3) Cell Separation Performance Evaluation

The nonwoven fabric pile was washed with physiological saline in an amount about 6 times the volume of the filter for separating stem cell. Then, in an incubator at 37° C., 8 ml of the subcutaneous adipocyte tissue-derived enzyme-treated fluid was passed through the filter at a flow rate of 0.5 ml/min using a syringe pump. Then, 2.5 ml of physiological saline was passed through the filter in the same direction at the same flow rate to thereby wash away the tissue-derived impurities remaining in the cell filter, including the enzyme used for disintegration, fat droplets, erythrocytes, leukocytes and platelets. Thereafter, 4 ml of a cell culture medium (α-MEM) containing 15% of fetal bovine serum was caused to flow swiftly in the direction reverse to the direction of the flow of the enzyme-treated fluid to thereby recover the desired cell fraction.

The cell recovery rate was calculated by dividing the number of nucleated cells in the recovered fluid by the number of nucleated cells before passage through the filter. The cell passage rate was calculated by dividing the number of nucleated cells after passage through the filter by the number of nucleated cells before passage through the filter. The "nucleated cells" so referred to herein are cells having a structure such that a nucleus is surrounded by a cell membrane. More specifically, they may be stem cells, vascular endothelial cells, smooth muscle cells, pericytes and the like, with erythrocytes, platelets and mature fatty cells being excluded. The nucleated cell count was determined using a hemocytometer after lysis of erythrocytes contained in the fluid with ammonium chloride. For determining the erythrocyte and platelets removal rates, the erythrocytes and platelets contained in the fluid before passage through the filter and in the recovered fluid were counted using an automated blood cell counter (Sysmex K-4500). As a result, the rate of recovery of nucleated cells was 82%, and the erythrocyte and platelet counts in the recovered fluid were below the respective detection limits (Tables 5, 6, 7).

These data indicate that the filter for separating stem cell makes it possible to recover nucleated cells in high yields while removing most of erythrocytes and platelets.

Then, the fluid before passage (8 ml) and the recovered fluid (about 4 ml) were centrifuged (1,200 rpm, 5 minutes) to cause cells to settle. Each supernatant was discarded and each cell mass was resuspended in 8 ml of a growth medium (α-MEM containing 15% of fetal bovine serum), and each suspension was distributed, in 1-μl portions, into polystyrene culture dishes (ø60 mm) containing a growth medium. Cultivation was carried out in an incubator at 37° C. in the presence of 5% $CO_2$ for 9 days, and the colonies formed were stained with 0.5% (w/v) crystal violet and counted (FIG. 4). As a result, the colony formation percentage was 61% as compared with the fluid before passage. This indicated that colony-forming cells can be recovered in high yields using this separating filter.

Then, the proportions of cell populations and fine impurity particles contained in the fluid before passage, the recovered fluid and the washings-containing fluid after passage were determined using a flow cytometer (BD FACSCanto) (FIG. 5). In FIG. 5, P1 indicates a cell population containing fat-derived stem cells, P2 indicates a cell population mainly composed of leukocytes, and P3 indicates tissue-derived impurities such as fat droplets. As a result, in the recovered fluid (FIG. 5B: P1/P2=7.81), the proportion of the fraction (P1) abundant in fat-derived stem cells was higher and the proportion of the fraction (P2) abundant in leukocytes was lower as compared with the fluid before passage (FIG. 5A: P1/P2=5.13). In the washings-containing fluid after passage (FIG. 5C: P1/P2=0.66), the proportion of the fraction abundant in leukocytes was very high and the proportion of tissue-derived impurities, presumably fat droplets and the like, was very high (FIG. 5C: P3 area). These results revealed that fat-derived stem cells could be selectively captured and recovered by using the filter for separating stem cell while leukocytes were partly removed. Furthermore, in the washings-containing fluid after passage, the proportion of the fraction abundant in leukocytes was very high and the proportion of tissue-derived impurities, presumably fat droplets and the like, was very high, indicating that these impurities had substantially passed through the filter and been removed.

(4) Evaluation of the Ability to Differentiate into Fat

The fat-derived cells contained in the recovered fluid mentioned above under (3) were cultured in a growth medium in an incubator at 37° C. in the presence of 5% $CO_2$ for several days. Thereto were added three additives promoting the induction of differentiation into fat (hydrocortisone: Sigma, isobutylmethylxanthine: Sigma, and indomethacin: Sigma) to respective concentrations of 0.1 μM, 0.5 mM and 50 μg/ml to induce the differentiation into fat. In a parallel control run, those additives were not added (Control 1). As a result, accumulations of fat droplets were observed in the cells induced to differentiate, as shown in FIG. 6, upper row. It was thus confirmed that the fat-derived cells captured and recovered by using the filter for separating stem cell had the ability to differentiate into fat.

(5) Evaluation of the Ability to Differentiate into Bone

The fat-derived cells in the recovered fluid were cultured in the same manner as mentioned above under (4) and, then, three additives promoting the induction of differentiation into bone (β-glycerophosphate: Calbiochem, ascorbic acid phosphate: Wako, dexamethasone: Sigma) were added thereto to respective concentrations of 10 mM, 50 FL g/ml and 100 nM to induce the differentiation into bone. In a parallel control run, the additives were not added (Control 2). Medium exchange was carried out at 3-day intervals and, after 2 weeks, alizarin red staining was carried out as an indicator of differentiation into bone. As a result, the control cells were negative to alizarin red staining, while the cells induced to differentiate into bone gave positive results, as shown in FIG. 6, lower row. It was thus confirmed that the fat-derived cells captured and recovered by using the filter for separating stem cell had the ability to differentiate into bone.

Based on the results mentioned above under (4) and (5), it was confirmed that there were biological tissue-derived stem cells abundantly among the fat-derived cells separated and recovered by using the filter for separating stem cell of Example 7.

Example 8

Following the procedure of Example 7 in the same manner except that the filter for separating stem cell used contained nonwoven fabrics made of rayon and polyolefin [density K (basis weight (g/m²)/thickness (m)=$1.5 \times 10^5$ ($110/(7.4 \times 10^{-4})$), fiber diameter=15±9 μm, mesh opening=5 to 48 μm] as the material for separating stem cell, the rate of recovery of nucleated cells, the erythrocyte/platelet removal rates and the colony formation rate were determined. As a result, the nucleated cell recovery rate attained with the filter for separating stem cell was 53%, the erythrocyte and platelet levels in the recovered fluid were below the respective detection limits, and the colony formation rate was 74% as compared with the control (Tables 5, 6, 7).

The fat-derived cells contained in the recovered fluid were cultured in the same manner as in Example 7, (4) and (5), and induced to differentiate into fat or bone, whereupon accumulations of fat droplets and alizarin red positiveness could be confirmed (FIG. 6).

Flow cytometer analysis gave the same results as in Example 7.

Example 9

Following the procedure of Example 7 in the same manner except that the filter for separating stem cell used contained nonwoven fabrics made of polyester [density K (basis weight (g/m$^2$)/thickness (m)=5.9×10$^4$ (200/(3.4× 10$^{-3}$)), fiber diameter=14±8 μm, mesh opening=7 to 100 μm) as the material for separating stem cell, the rate of recovery of nucleated cells, the erythrocyte/platelet removal rates and the colony formation rate were determined. As a result, the nucleated cell recovery rate attained with the filter for separating stem cell was 59%, the rate of passage thereof was 25%, the erythrocyte and platelet levels in the recovered fluid were below the respective detection limits, and the colony formation rate was 60% as compared with the control (Tables 5, 6, 7). The cells obtained by cultivation were induced to differentiate into bone; alizarin red staining was positive. Flow cytometer analysis gave the same results as in Example 7.

Example 10

Following the procedure of Example 7 in the same manner except that the filter for separating stem cell used contained nonwoven fabrics made of polyester [density K (basis weight (g/m$^2$)/thickness (m)=1.6×10$^5$ (85/(5.3× 10$^{-4}$)), fiber diameter=12±2 μm, mesh opening=10 to 26 μm) as the material for separating stem cell, the rate of recovery of nucleated cells, the erythrocyte/platelet removal rates and the colony formation rate were determined. As a result, the nucleated cell recovery rate attained with the filter for separating stem cell was 30%, the rate of passage thereof was 45%, the erythrocyte and platelet levels in the recovered fluid were below the respective detection limits, and the colony formation rate was 45% as compared with the control (Tables 5, 6, 7). The cells obtained by cultivation were induced to differentiate into bone; alizarin red staining was positive.

Comparative Example 6

Following the procedure of Example 7 in the same manner except that the filter for separating stem cell used contained nonwoven fabrics made of polypropylene [density K (basis weight (g/m$^2$)/thickness (m)=1.1×10$^6$ (1100/(1.0× 10$^{-4}$)), fiber diameter=8±3 μm, mesh opening=3 to 20 μm) as the material for separating stem cell, the rate of recovery of nucleated cells, the erythrocyte/platelet removal rates and the colony formation rate were determined. As a result, the nucleated cell recovery rate attained with the filter for separating stem cell was 42%, the erythrocyte and platelet levels in the recovered fluid were below the respective detection limits, and the colony formation rate was 39% as compared with the control (Tables 5, 6, 7).

Comparative Example 7

Following the procedure of Example 7 in the same manner except that the filter for separating stem cell used contained nonwoven fabrics made of cotton [density K (basis weight (g/m$^2$)/thickness (m)=8.3×10$^3$ (25/(3.0× 10$^{-3}$)), fiber diameter=11±4 μm, mesh opening=3 to 25 μm) as the material for separating stem cell, the rate of recovery of nucleated cells, the erythrocyte/platelet removal rates and the colony formation rate were determined. As a result, the nucleated cell recovery rate attained with the filter for separating stem cell was 29%, the erythrocyte and platelet levels in the recovered fluid were below the respective detection limits, and the colony formation rate was 30% as compared with the control (Tables 5, 6, 7).

Comparative Example 8

Following the procedure of Example 7 in the same manner except that the filter for separating stem cell used contained nonwoven fabrics made of polypropylene [density K (basis weight (g/m$^2$)/thickness (m)=8.3×10$^3$ (30/(3.6× 10$^{-3}$)), fiber diameter=11±4 μm, mesh opening=3 to 25 μm) as the material for separating stem cell, the rate of recovery of nucleated cells, the erythrocyte/platelet removal rates and the colony formation rate were determined. As a result, the nucleated cell recovery rate attained with the filter for separating stem cell was 5%, the erythrocyte and platelet levels in the recovered fluid were below the respective detection limits, and the colony formation rate was 5% as compared with the control (Tables 5, 6, 7).

Comparative Example 9

An experiment was carried out following the procedure of Example 7 in the same manner except that the filter for separating stem cell used contained nonwoven fabrics made of polyester [density K (basis weight (g/m$^2$)/thickness (m)=2.3×10$^5$ (80/(3.5×10$^{-4}$)), fiber diameter=2.3±0.5 μm, mesh opening=2 to 13 μm) as the material for separating stem cell. However, clogging occurred after passage of 70% of the fluid enzymatically treated for disintegration, hence no evaluation could be made.

[Example 11] Separation of Biological Tissue-Derived Stem Cells from Subcutaneous Fat Using a Material for Separating Stem Cell (1) Preparation of a Concentrated Subcutaneous Adipocyte Tissue-Derived Cell Suspension Separately from Examples 7 to 10 and Comparative Examples 6 to 9 mentioned above, a rabbit (Japanese albino) weighing 3.5 kg was euthanized by excess administration of Ketalar/Selactar, and 50 g of dorsal subcutaneous fat was collected. This white fat was minced with surgical scissors and then shaken with 100 mL of 0.075% (w/v) collagenase/ phosphate buffered saline (pH=7.4) at 37° C. (1 hour). A portion corresponding to 3 g of fat was taken from this enzyme-treated fluid and centrifuged (1,200 rpm, 5 minutes) to cause the cell population contained therein to settle. After removal of the supernatant, the cell mass was suspended in 1 ml of α-MEM medium; a concentrated cell suspension was thus prepared.

(2) Preparation of a Filter for Separating Stem Cell

A filter for separating stem cell was prepared by putting together 24 piled-up nonwoven fabrics made of rayon and polyolefin (polyethylene-polypropylene blend) [density K (basis weight (g/m$^2$)/thickness (m)=1.6×10$^5$ (95/(5.9× 10$^{-4}$)), fiber diameter=15±9 μm, mesh opening=5 to 48 μm) from top to bottom by means of a stopper with an outside diameter of 12 mm, an inside diameter of 7 mm and a height of 5 mm and inserting the pile, as a material for separating stem cell, into a cylindrical tube having an inside diameter of 20 mm and equipped with an inlet and an outlet for fixation of the material for separating stem cell.

(3) Cell Separation Performance Evaluation

The nonwoven fabric pile was washed with physiological saline in an amount about 6 times the volume of the filter for separating stem cell. Then, 1 ml of the above-mentioned concentrated suspension was passed through the filter at room temperature at a flow rate of 1 ml/min using a syringe pump. Then, 4 ml of phosphate buffer was passed through the filter in the same direction at the same flow rate to thereby wash away the unnecessary matters remaining in the filter for separating stem cell and, then, 24 ml of phosphate buffer was caused to flow swiftly in the direction reverse to the direction of the flow of the enzyme-treated fluid to thereby recover the desired cell fraction.

The cell recovery rate was calculated by dividing the number of nucleated cells in the recovered fluid by the number of nucleated cells before passage through the filter. The nucleated cell count was determined using a hemocytometer after lysis of erythrocytes contained in the fluid with ammonium chloride. For determining the erythrocyte and platelets removal rates, the erythrocytes and platelets contained in the fluid before passage through the filter and in the recovered fluid were counted using an automated blood cell counter (Sysmex K-4500). As a result, the rate of recovery of nucleated cells was 66%, and the erythrocyte and platelet removal rates were 88% and 86%, respectively. The colony formation rate as compared with the fluid before passage was 70%.

Example 12

Following the procedure of Example 11 in the same manner except that the filter for separating stem cell used contained nonwoven fabrics made of rayon and polyolefin (polyethylene-polypropylene blend) [density K (basis weight $(g/m^2)$/thickness $(m)=1.5\times10^5$ $(110/(5.63\times10^{-4}))$, fiber diameter=$15\pm9$ μm, mesh opening=5 to 48 μm) as the material for separating stem cell, the rate of recovery of nucleated cells, the erythrocyte/platelet removal rates and the colony formation rate were determined. As a result, the nucleated cell recovery rate attained with the filter for separating stem cell was 69%, the erythrocyte and platelet removal rates were 93% and 75%, respectively, and the colony formation rate was 75% as compared with the control.

The nucleated cell recovery rates and colony formation rates found in Examples 7 to 12 and Comparative Examples 6 to 9 mentioned above are summarized in Table 5. In making comprehensive evaluations, the case where the colony formation rate was 60% or higher and the nucleated cell recovery rate was 60% or higher was given "Excellent", the case where the colony formation rate was not lower than 40% was given "Fair", the case where the colony formation rate was lower than 40% was given "Poor", and the case where the colony formation rate was lower than 20% or clogging occurred was given "Bad". The erythrocyte removal rates and platelet removal rates are summarized in Tables 6 and 7, respectively.

The rabbit subcutaneous adipocyte tissue (before treatment) used in the examples is shown in FIG. 2; the rabbit subcutaneous adipocyte tissue-derived treated fluid used in the examples is shown in FIG. 3; the results of colony forming ability testing of the cells contained in the fluid before passage used in the examples and comparative examples and in the recovered fluids in Examples 7 and 8 and Comparative Examples 6 to 8 are shown in FIG. 4; the results of flow cytometer analyses of the fluid before passage (A), the recovered fluid (B) and the washings-containing fluid after passage (C) used or obtained in Example 7 are shown in FIG. 5 (P1: cell population containing fat-derived stem cells; P2: cell population mainly consisting of leukocytes; P3: fat droplets and other tissue-derived impurities); and the manners of differentiation of the tissue-derived cells in the recovered fluids in Examples 7 and 8 into adipocytes (upper row, left: Control 1 in Example 7, middle: cells treated for differentiation induction in Example 7, right: cells treated for differentiation induction in Example 8) or bone (lower row, left: Control 2 in Example 7, middle: cells treated for differentiation induction in Example 7, right: cells treated for differentiation induction in Example 8) are shown in FIG. 6.

TABLE 5

Nucleated cell recovery rates, passage rates, colony formation rates and comprehensive evaluations

| | Nucleated cell recovery rate | Passage rate | Colony formation rate | Comprehensive evaluation |
|---|---|---|---|---|
| Example 7 | 82% | 3% | 61% | Excellent |
| Example 8 | 53% | 20% | 74% | Fair |
| Example 9 | 59% | 25% | 60% | Fair |
| Example 10 | 30% | 45% | 45% | Fair |
| Example 11 | 66% | 3% | 70% | Excellent |
| Example 12 | 69% | 6% | 75% | Excellent |
| Comp. Ex. 6 | 42% | 20% | 39% | Poor |
| Comp. Ex. 7 | 29% | 36% | 30% | Poor |
| Comp. Ex. 8 | 5% | 4% | 5% | Bad |
| Comp. Ex. 9 | Clogging | ← | ← | Bad |

TABLE 6

Erythrocyte counts

| | Fluid before passage | Recovered fluid |
|---|---|---|
| Fluid before passage through filter | $2 \times 10^4/\mu l$ | — |
| Example 7 | ↑ | Below detection limit |
| Example 8 | ↑ | Below detection limit |
| Example 9 | ↑ | Below detection limit |
| Example 10 | ↑ | Below detection limit |
| Comp. Ex. 6 | ↑ | Below detection limit |
| Comp. Ex. 7 | ↑ | Below detection limit |
| Comp. Ex. 8 | ↑ | Below detection limit |
| Fluid before passage through filter | $28.3 \times 10^4/\mu l$ | — |
| Example 11 | ↑ | $3.3 \times 10^4/\mu l$ |
| Example 12 | ↑ | $2.0 \times 10^4/\mu l$ |

TABLE 7

Platelet counts

| | Fluid before passage | Recovered fluid |
|---|---|---|
| Fluid before passage through filter | $0.5 \times 10^4/\mu l$ | — |
| Example 7 | ↑ | Below detection limit |
| Example 8 | ↑ | Below detection limit |
| Example 9 | ↑ | Below detection limit |
| Example 10 | ↑ | Below detection limit |
| Comp. Ex. 6 | ↑ | Below detection limit |
| Comp. Ex. 7 | ↑ | Below detection limit |
| Comp. Ex. 8 | ↑ | Below detection limit |
| Fluid before passage through filter | $8.4 \times 10^4/\mu l$ | — |
| Example 11 | ↑ | $1.2 \times 10^4/\mu l$ |
| Example 12 | ↑ | $2.1 \times 10^4/\mu l$ |

The above results indicate that, by using the materials for separating stem cell according to the invention, it is possible to selectively separate biological tissue-derived multipotent stem cells efficiently and in a very simple and easy manner, without using a centrifuge or the like. It is also evident that, by using the materials for separating stem cell according to the invention, it is possible to provide highly pure cells substantially free of fat droplets, erythrocytes, leukocytes, platelets and other tissue-derived impurities, the enzyme used for disintegration, etc.

INDUSTRIAL APPLICABILITY

By using the material for separating stem cell and filter for separating stem cell according to the invention, it becomes possible to separate and recover adherent stem cells capable of differentiating into various cells or organs, in a condition almost free of erythrocytes, leukocytes and platelets, in a simple and easy manner from such a body fluid as bone marrow fluid, peripheral blood or umbilical cord blood. Further, by using the material for separating stem cell and filter for separating stem cell according to the invention, it becomes possible to separate and recover biological tissue-derived stem cells capable of differentiating into various cells or organs, in a condition substantially free of tissue-derived impurities such as fat droplets, erythrocytes, leukocytes and platelets and of the enzyme or enzymes used for disintegration, among others, in a simple and easy manner from a biological tissue-derived treated fluid. Furthermore, the adherent stem cells and biological tissue-derived stem cells obtained by using the material for separating stem cell and filter for separating stem cell are useful as therapeutic cells for use in revascularization, tissue enlargement and like regenerative medicine and cellular medicine techniques.

Further, the stem cells recovered by the separation method using a filter for separating stem cell containing the material for separating stem cell according to the invention as packed therein can be used as such or can be amplified in a closed system and, therefore, such filter can be provided as a filter for preparing therapeutic cells for use in regenerative medicine or cellular medicine, for example in heart muscle regeneration or revascularization. Furthermore, by using the filter for separating stem cell, it becomes possible to provide stem cells very useful as a cell source for regenerative medicine and hardly causative of adverse reactions, with a very low percentage of coexisting fat droplets, erythrocytes, leukocytes, platelets and other contaminants. By integrating a culture bag with the filter for separating stem cell, highly safe stem cells for therapeutic uses can be prepared in a closed system encompassing cell collection to amplification.

Figure 1:
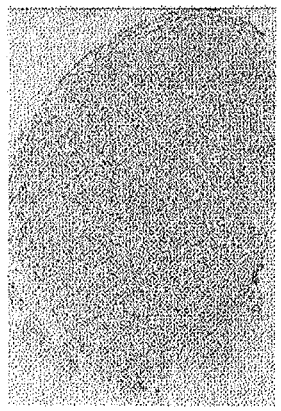
FIG. 1 This figure shows the cartilage formation evaluation results obtained in Examples 1 to 5, Comparative Example 3 and Reference Example 1.
Figure 1:
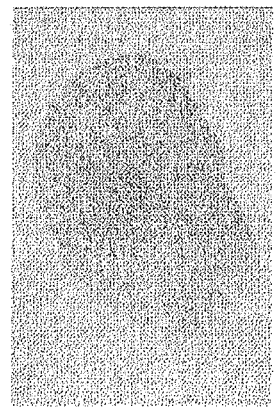
Figure 1:
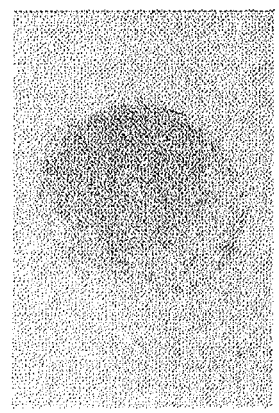
Figure 1:
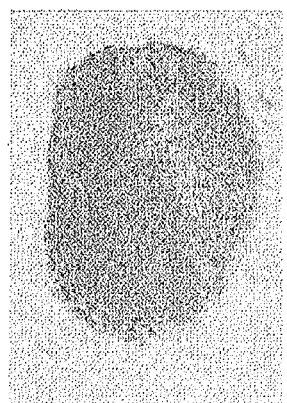
Figure 1:
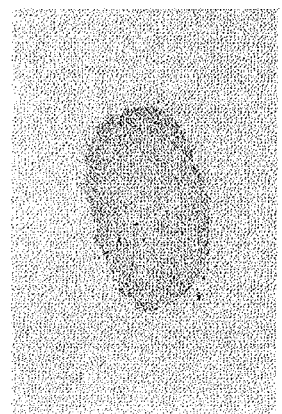
Figure 1:
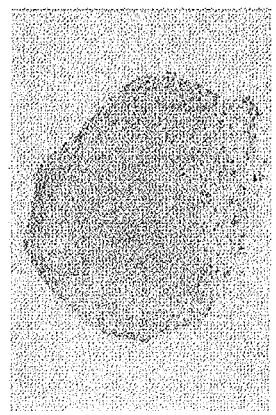
Figure 1:
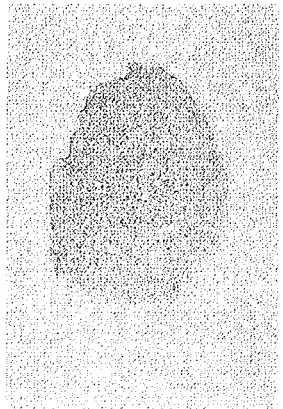
Figure 2:
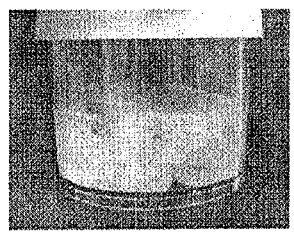
FIG. 2 This figure shows the rabbit subcutaneous adipocyte tissue (before treatment) used in the examples.
Figure 3:
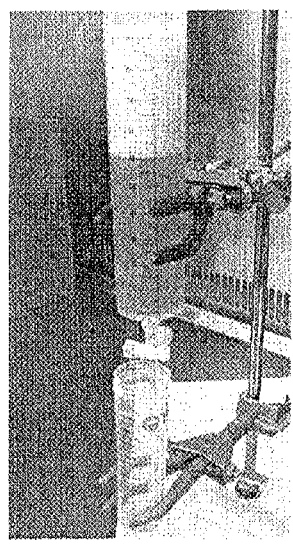
FIG. 3 This figure shows the rabbit subcutaneous adipocyte tissue-derived treated fluid used in the examples.
Figure 4:
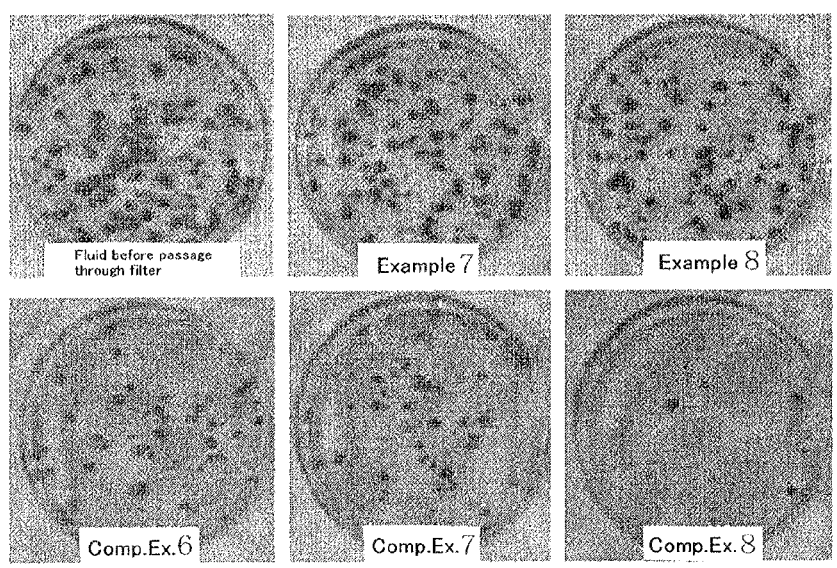
FIG. 4 This figure shows the results of colony forming ability testing of the cells contained in the fluid before passage as used in the examples and comparative examples and in the recovered fluids in Example 7 and 8 and Comparative Examples 6 to 8, respectively.
Figure 5:
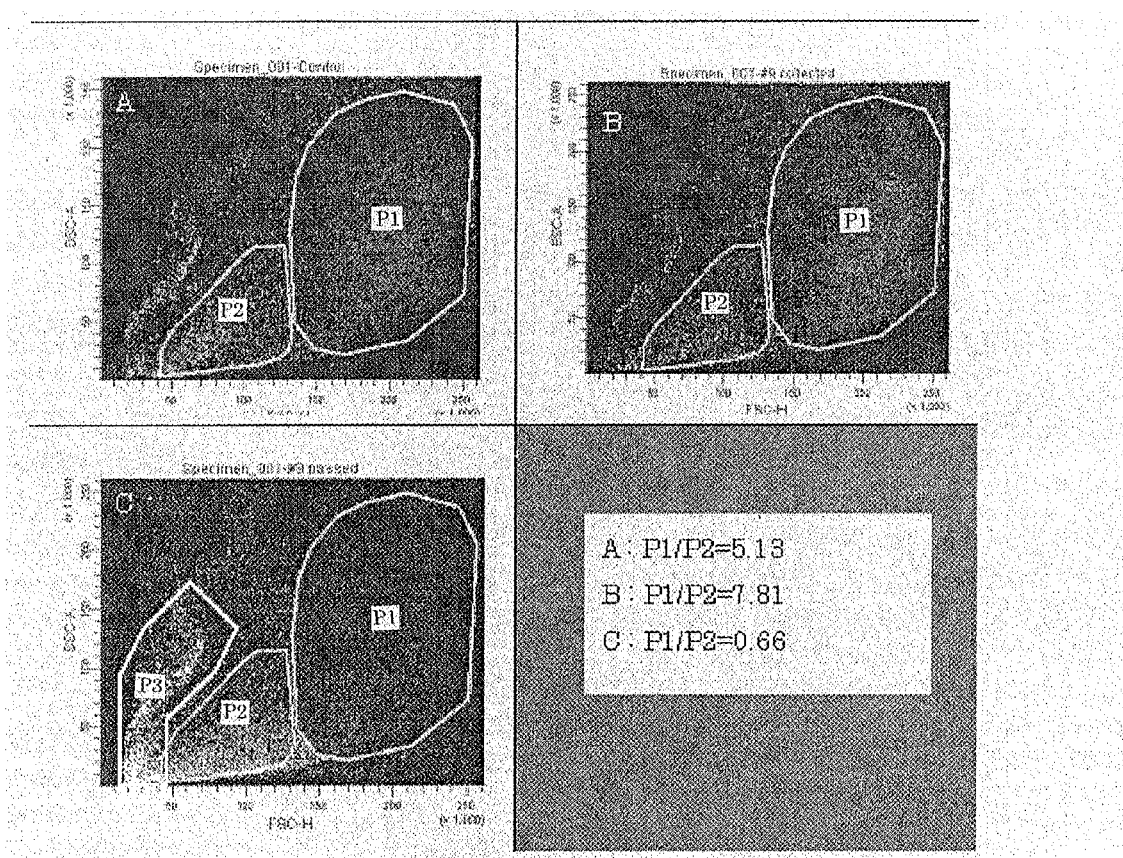
FIG. 5 This figure shows the results of flow cytometer analyses of the fluid before passage (A), the recovered fluid (B) and the washings-containing fluid after passage (C) in Example 7.
Figure 6:
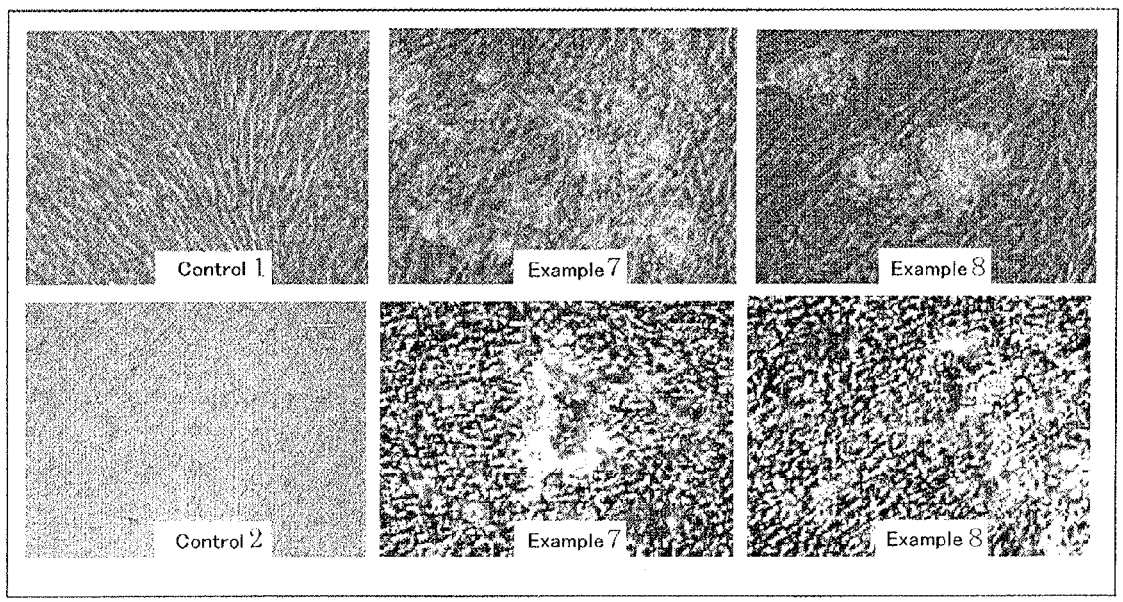
FIG. 6 This figure shows the manners of differentiation of the tissue-derived cells in the recovered fluids in Examples 7 and 8 into adipocytes and bone, respectively.

The invention claimed is:

1. A filter for separating stem cells which comprises a material for separating stem cells which has a density K of $1.0 \times 10^4 \text{ g/m}^3 < K < 1.0 \times 10^6 \text{ g/m}^3$ and a fiber diameter of 5 um to 30 um,
   which is made of combination of fibers of two or more synthetic polymer species in combination, and having mesh openings which are substantial pores formed by crossing two or more different fibers,
   wherein a minor axis of each mesh opening is not shorter than 5 µm and a major axis thereof is not longer than 80 µm, and
   which has the form of a nonwoven fabric,
   wherein the combination of fibers of two or more synthetic polymer species is a combination of rayon and a polyolefin, and wherein the material for separating stem cells is packed in a container having a fluid inlet port and a fluid outlet port.

2. The filter for separating stem cells according to claim 1, wherein the fibers of synthetic polymer species is split fiber or conjugated fiber.

3. The filter for separating stem cells according to claim 1, which has a density K of $1.0 \times 10^4 < K < 2.0 \times 10^5 \text{ g/m}^3$.

4. The filter for separating stem cells according to claim 1, wherein a washing fluid inlet is provided at the fluid inlet port or on the fluid inlet side other than the fluid inlet port for washing away unnecessary cells and other unnecessary substances remaining in the material for separating stem cell and a cell recovering fluid inlet is provided at the fluid outlet port or at a site on the fluid outlet side other than the fluid outlet port for recovering cells captured by the material for separating stem cells.

5. The filter for separating stem cells according to claim 4 wherein a bag for receiving and storing a cell recovering fluid containing cells captured by the material for separating stem cells is provided at the fluid inlet port or washing fluid inlet or at a site on the fluid inlet side other than the fluid inlet port or washing fluid inlet.

6. The filter for separating stem cells according to claim 5, wherein the bag for receiving and storing a cell recovering fluid containing cells captured by the material for separating stem cells is a bag for cell culture.

* * * * *

UNITED STATES PATENT AND TRADEMARK OFFICE
CERTIFICATE OF CORRECTION

PATENT NO. : 9,708,581 B2  
APPLICATION NO. : 14/063407  
DATED : July 18, 2017  
INVENTOR(S) : Akira Kobayashi et al.

Page 1 of 1

It is certified that error appears in the above-identified patent and that said Letters Patent is hereby corrected as shown below:

Claim 1, Column 34, Line 15; delete "$1.0 \times 10^4$ g/m$^3$ < K < $1.0 \times 10^6$ g/m$^3$ and a fiber diameter of 5 um to 30 um,"; insert --$1.0 \times 10^4$ g/m$^3$ $\leqq$ K $\leqq$ $1.0 \times 10^6$ g/m$^3$ and a fiber diameter of 5 μm to 30 μm,--;

Claim 3, Column 34, Line 34; delete "1, which has a density K of $1.0 \times 10^4$ < K < $2.0 \times 10^5$ g/m$^3$"; insert --which has a density K of $1.0 \times 10^4$ $\leqq$ K $\leqq$ $2.0 \times 10^5$ g/m$^3$--.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*